United States Patent
Kim et al.

(10) Patent No.: US 10,639,343 B2
(45) Date of Patent: May 5, 2020

(54) **PREPARATION METHOD OF *GYNOSTEMMA PENTAPHYLLUM* LEAVES EXTRACT AND *GYNOSTEMMA PENTAPHYLLUM* EXTRACT PREPARED BY THE METHOD THEREOF**

(71) Applicant: BTC CORPORATION, Ansan-si (KR)

(72) Inventors: Tae Young Kim, Ansan-si (KR); Joo Myung Moon, Ansan-si (KR); Su Hyun Kyong, Anyang-si (KR); Yoon Hee Kim, Ansan-si (KR)

(73) Assignee: BTC CORPORATION, Gyeonggi-Do (KR)

( * ) Notice: Subject to any disclaimer, the term of this patent is extended or adjusted under 35 U.S.C. 154(b) by 69 days.

(21) Appl. No.: 15/862,131

(22) Filed: Jan. 4, 2018

(65) Prior Publication Data
US 2019/0201468 A1 Jul. 4, 2019

(51) Int. Cl.
*A61K 36/424* (2006.01)

(52) U.S. Cl.
CPC ........ *A61K 36/424* (2013.01); *A61K 2236/17* (2013.01); *A61K 2236/33* (2013.01); *A61K 2236/331* (2013.01)

(58) Field of Classification Search
None
See application file for complete search history.

(56) References Cited

U.S. PATENT DOCUMENTS

| | | | | |
|---|---|---|---|---|
| 2008/0260877 | A1* | 10/2008 | Bai | A23F 3/00 424/758 |
| 2011/0015142 | A1 | 1/2011 | Huh et al. | |
| 2012/0171309 | A1* | 7/2012 | Amagase | A61K 36/424 424/725 |
| 2019/0000905 | A1* | 1/2019 | Moon | A61K 36/424 |
| 2019/0070240 | A1* | 3/2019 | Wang | A61P 19/02 |
| 2019/0110980 | A1* | 4/2019 | Park | A61K 8/63 |

FOREIGN PATENT DOCUMENTS

| | | | |
|---|---|---|---|
| CN | 102579471 A | * | 7/2012 |
| CN | 101803799 A | * | 11/2012 |
| CN | 105998144 A | * | 10/2016 |
| KR | 100930580 | | 12/2009 |
| KR | 101200571 | | 11/2012 |
| KR | 20140108621 | | 9/2014 |
| KR | 20170079903 | | 7/2017 |

OTHER PUBLICATIONS

Gauhar, R. et al. Heat Processed G. pentaphyllum Extract Improves Obesity in ob/ob Mice by Activating AMP Activated Protein Kinase. Biotechnology Letters 34(9)1607-1616, 2012. (Year: 2012).*

Ban, et al., Optimization of the Manufacturing Process for Black Ginseng, Journal of the Korean Society for Applied Biological Chemistry, 2010, pp. 71-77.
Piao, et al., Dammarane-type saponins from heat-processed Gynostemma pentaphyllum show fortified activity against A549 cells, Archives of Pharmacal Research, 2013, pp. 874-879.
Yeo, et al., Potential Hypoglycemic Effect of an Ethanol Extract of Gynostemma pentaphyllum in C57BL/KsJ-db/db Mice, Journal of Medicinal Food, 2008, pp. 709-716.
Baur, et al., Resveratrol improves health and survival of mice on a high-calorie diet, Nature, 2006, pp. 337-342.
Bonaldo, et al., Cellular and molecular mechanisms of muscle atrophy, Disease Models & Mechanisms, 2013, pp. 25-39.
Chen, et al., Metabolic profiling of Gynostemma pentaphyllum extract in rat serum, urine and faeces after oral administration, Journal of Chromatography B, 2014, pp. 1-31.
Han, et al., Change of mTOR, p70S6K, 4E-BP1, and AMPK protein expressions with a intensive endurance exercise in rats, Korean Journal of Sports Science, 2011, pp. 1551-1561.
Hornberger, Mechanotransduction and the Regulation of mTORC1 Signaling in Skeletal Muscle, Int J Biochem Cell Biol., 2011, pp. 1267-1276.
Hwang, et al., Beneficial effectes of B-sitosterol on glucose and lipid metabolism in L6 myotube cells are mediated by AMP-activated protein kinase, Biochemical and Biophysical Research Communications, 2008, pp. 1253-1258.
Hwang, et al., Isodihydrocapsiate stimulates plasma glucose uptake by activation of AMP-activated protein kinase, Biochemical and Biophysical Research Communications, 2008, pp. 289-293.
Kim, et al., Bitter Melon (*Momordica charantia*) Extract Enhances Exercise Capacity in Mouse Model, Korean Journal of Food and Nutrition, 2016, pp. 506-512.
Lagouge, et al., Resveratrol Improves Mitochondrial Function and Protects against Metabolic Disease by Activating SIRT1 and PGC-1a, Cell, 2006, pp. 1109-1122.
Park, et al., Resveratrol stimulates glucose transport in C2C12 myotubes by activating AMP-activated protein kinase, Experimental and Molecular Medicine, vol. 39, 2007, pp. 222-229.

\* cited by examiner

*Primary Examiner* — Ralph J Gitomer

(74) *Attorney, Agent, or Firm* — Cantor Colburn LLP

(57) ABSTRACT

A preparation method of *Gynostemma Pentaphyllus* leaves extracts with increased amount of small molecular effective saponin and decreased benzopyrene includes the steps of drying fresh *Gynostemma Pentaphyllus* leaves after heating, treating the dried *Gynostemma Pentaphyllus* leaves with steam, adding water of 1 to 100-fold volume to the above *Gynostemma Pentaphyllus* leaves and then preparing a hot water extract by carrying out a hot water extraction at 100-180 V, 0.5-10 atm for 1-120 hours, adding $C_1$-$C_4$ lower alcohol of 1 to 100-fold volume to the residual remained after the hot water extraction and then preparing an alcohol extract of the residual from the hot water extract by carrying out an alcohol extraction at 50-100° C. for 1-4 hours, and mixing the hot water extract and the alcohol extract, and then filtering and concentrating the mixture.

11 Claims, 14 Drawing Sheets

PREPARATION METHOD OF *GYNOSTEMMA PENTAPHYLLUM* LEAVES EXTRACT AND *GYNOSTEMMA PENTAPHYLLUM* EXTRACT PREPARED BY THE METHOD THEREOF

TECHNICAL FIELD

The present invention relates to a preparation method of *Gynostemma Pentaphyllum* leaves extracts with increased small molecular effective saponin contents and decreased benzopyrene contents.

BACKGROUND

A study on the effect of *Gynostemma Pentaphyllum* leaves extracts reported that an ethanol extract of *Gynostemma Pentaphylluim* leaves showed potent hypoglycemic effect in animal model of type 2 diabetes, and was effective at the amount of 100 mg/kg [Reference material: Yeo J Y, et al., 2008, Potential Hypoglycemic Effect of an EtOH Extract of *Gynostemma pentaphyllum* in C57BL/KsJ-db/db Mice, J. Medicinal Food, 11: 709-716].

Further, *Gynostemma Pentaphyllum* leaves extracts has been suggested to improve metabolic disease including obesity, diabetes, and hyperlipidemia, etc. by increasing the activity of AMP-activated protein kinase (AMPK), and as a major preparation method of such a *Gynostemma Pentaphyllum* leaves extract, an extraction method increasing the contents of damulin A and B through ethanol extraction and subsequent high temperature treatment is known (Korean Patent No. 10-0930580). Another example is Korean Patent Publication No. 10-2014-0108621 relates to a composition for the treatment or prevention of type 2 diabetes, obesity, or hyperlipidemia, comprising gypenoside extract of *Gynostemma Pentaphyllum* leaves containing one or more dammarane triterpenoid saponin compounds selected from the group consisting of gypenoside UL1, gypenoside UL2, gypenoside UL3, gypenoside UL4, gypenoside UL5, gypenoside UL6, gypenoside UL7, and gypenoside XLVIII, as an active ingredient.

It is known that the efficacy of saponin increase when saponin is converted to small molecular saponin. Various methods such as fermentation, enzyme or heat treatment, etc. have been reported for the conversion to small molecular effective saponin. However, if the fresh leaves of *Gynostemma Pentaphyllus* are used as is, the precursors of small molecular effective saponin, which are diversely present in the fresh leaves, are not sufficiently activated. Thus, if the leaves are extracted according to such a method, the efficacy of the extract would be low, and it has been confirmed by years of researches that even if the processes such as heat treatment, etc. are carried out after extraction, the efficacy would not be guaranteed. Further, if the leaves are fermented or treated with enzyme, small molecular effective saponin content increases to some extent; however, the process time and cost of production increase due to the additional process.

Benzopyrene is generated during the preparation process of the *Gynostemma Pentaphyllus* leaves extracts. Benzopyrene is a yellow crystalline solid which belongs to polycyclic aromatic hydrocarbon (PAH) and is produced by incomplete combustion at 300~600° C. Benzopyrene typically exists in coal tar, car exhaust emission, cigarette smoke, etc., emitted into the environment through incomplete combustion, and can spread far from the source of origin due to its high stability in the atmosphere. Benzopyrene also presents in the uncooked or unprocessed foods such as agricultural products, fishes and shells, etc., and can be produced when heating foods at high temperature due to degradation of carbohydrate, protein, lipid, etc., which are the main ingredients of foods. As such, body is exposed to benzopyrene through contaminated water, foods, and atmosphere, and various benzopyrene metabolites metabolized in the body are known as causing cancer by adducting to DNAs.

Further, benzopyrene is even more problematic due to its long residual period and strong toxicity, and is in the center of world-wide attention as a possible carcinogen as well as an endocrine disruptor. Also in the food sector, problems have arisen from benzopyrene, and recently in Korea, benzopyrene has been detected in the processed ginseng products, etc. such as heat-treated red or black *ginseng*, etc. and thus, there is an increased interest in the technology of reducing benzopyrene.

Therefore, a novel method to reduce the amount of benzopyrene while increasing dammarane small molecular effective saponin compounds such as ginsenoside Rg3, gypenoside L, gypenoside LI, etc., which are the main active physiological ingredients of *Gynostemma Pentaphyllus* leaves extracts is required.

SUMMARY

The objective of the present invention is mainly focused on providing a preparation method of *Gynostemma Pentaphyllus* leaves extracts with increased amount of small molecular size and effective saponin such as ginsenoside Rg3, gypenoside L, and gypenoside LI, etc., and lowered amount of benzopyrene.

Other objective of the present invention is to provide *Gynostemma Pentaphyllus* leaves extracts in a form of dried powder, characterized in comprising 10 or less ppb benzopyrene (for example, in the range from 0.01 to 10 ppb).

Another objective of the present invention is to provide *Gynostemma Pentaphyllus* leaves extracts characterized in comprising 0.01~7 mg/g of ginsenoside Rg3, 1.5~70 mg/g of gypenoside L, and 1.5~70 mg/g of gypenoside LI.

In addition, another objective of the present invention is to provide a composition comprising *Gynostemma Pentaphyllus* leaves extract as an active ingredient.

In order to achieve the above objectives, the present invention provides a preparation method of *Gynostemma Pentaphyllus* leaves extracts with increased amount of small molecular effective saponin and decreased benzopyrene, which comprises the following steps: (1) drying fresh leaves of *Gynostemma Pentaphyllus* after roasting or steaming; (2) treating the dried *Gynostemma Pentaphyllus* leaves with steam; (3) adding water of 1-fold to 100-fold volume and then preparing a hot water extract by carrying out hot water extraction at 100-150° C., 0.5-10 atm for 1-120 hours; (4) adding $C_1$-$C_4$ lower alcohol of 1-fold to 100-fold volume to the residual from the hot water extraction and then preparing an alcohol extract of residual from the hot water extraction by carrying out alcohol extraction at 50-100° C. for 1-120 hours; and (5) mixing the hot water extract of step (3) and the alcohol extract of step (4), and then filtering and concentrating the mixture.

In one embodiment of the present invention, in step (1) above, fresh leaves of *Gynostemma Pentaphyllus* are dried after roasting or steaming at 90-180° C. for 1-120 hours by using electric heater.

In one embodiment of the present invention, the steam treatment in step (2) can be carried out at 100-130° C. for 0.5-10 hours.

In one embodiment of the present invention, after completing step (1) and step (2), the process of drying the above Gynostemma Pentaphyllus leaves again and treating them with steam can be added/repeated for 1-5 times.

In one embodiment of the present invention, the hot water of step (3) can be under acidic condition with pH 1-7.

In one embodiment of the present invention, an acid used to regulate pH of the hot water can be one or more selected from citric acid, butyric acid, hydrochloric acid, trifluoroacetic acid, trichloroacetic acid, acetic acid, vitamin C, malic acid, lactic acid, succinic acid, and alginate.

In one embodiment of the present invention, the $C_1$-$C_4$ lower alcohol of step (4) can be one or more selected from methanol, ethanol, propanol, isopropanol, and butanol, respectively.

In one embodiment of the present invention, the lower alcohol of step (4) can be aqueous alcohol solution with 10-95% (v/v), respectively.

The present invention further provides Gynostemma Pentaphyllus leaves extracts prepared by the above method, which comprises 0.01-7 mg/g of ginsenoside Rg3, 1.5-70 mg/g of gypenoside L, 1.5-70 mg/g of gypenoside LI, other small molecular effective saponin, and/or comprises 10 ppb or less benzopyrene.

The present invention also provides Gynostemma Pentaphyllus leaves extracts comprising 0.01-7 mg/g of ginsenoside Rg3, 1.5-70 mg/g of gypenoside L, 1.5-70 mg/g gypenoside LI, other small molecular effective saponin, and/or comprising 10 ppb or less benzopyrene.

The present invention further provides a composition comprising the above Gynostemma Pentaphyllus leaves extracts as an active ingredient. In one embodiment of the present invention, the composition comprising the above Gynostemma Pentaphyllus leaves extracts is a composition for the prevention or treatment/improvement of obesity, diabetes, or muscle loss or a composition for enhancing motor ability.

Furthermore, in one embodiment of the present invention, a composition comprising the above Gynostemma Pentaphyllus leaves extract as an active ingredient can be a pharmaceutical composition, a composition for food, a composition for health care food, a composition for quasi-drugs, etc.

DETAILED DESCRIPTION

Hereinafter, the present invention will be described in detail.

Gynostemma pentaphyllum is a perennial vine of the family Cucurbitaceae, which naturally grows in forests of mountains or fields. The Gynostemma pentaphyllum grows getting tangled by its rhizomes which extend to the side direction and have joints with white hair, but also climbs by its tendrils. In Korea, the habitat of Gynostemma pentaphyllum is mountain areas of southern region, Je-ju Island, Ul-leung Island, and outside of Korea, the Gynostemma pentaphyllum is widely distributed in China, Japan, Southeast Asia, etc. It grows mostly in the area with high humidity, such as coastal areas, riversides, etc.

Figure 12:
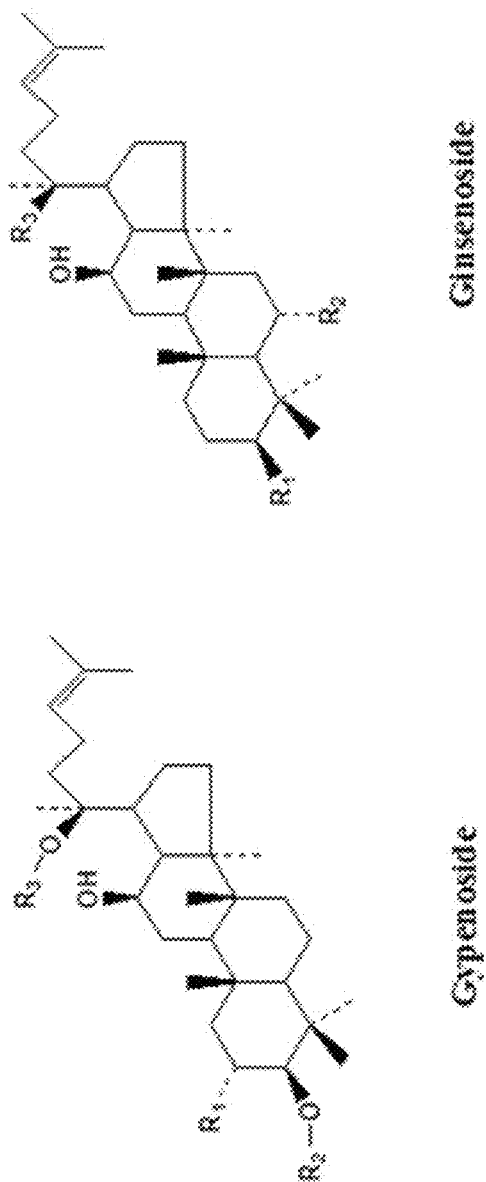
FIG. 12 shows a basic structure of gypenoside and ginsenoside.

Various species of Gynostemma pentaphyllum exist depending on the country and regions. Among the above, 30 Gynostemma species are known, and Pentapyllum is widely distributed among them, and its species, ingredients, and efficacy have been extensively studied. The Gynostemma pentaphyllum leaves contain various saponins, and these saponins are referred to as gynosaponin or gypenoside of which the structure is similar to ginsenoside compounds of red ginseng except the position to which OH is bound. The basic structure of gypenoside and ginsenoside is shown in FIG. 12.

The above saponins of the Gynostemma pentaphyllum leaves are known as to show efficacies such as improvement of lipid metabolism, defense action against cardiovascular disease, hypoglycemic action, action on central nerve system, anti-cancer action, inhibitory action on platelet aggregation, tonic action, etc. Further, the Gynostemma pentaphyllum leaf contains glycosides such as primeveroside, sophoroside, bisdesmoside, gentiobioside, rutinoside, etc., steroid, saccharides, pigments, etc. besides gypenoside, which is a type of saponin.

The mechanisms that reduce fat accumulation in the body can be largely classified into three mechanisms as follows:

The first mechanism inhibits accumulation of body fat by inhibiting the absorption of fat taken in from diet. Such a fat absorption can be inhibited by inhibiting lipase which breaks down the neutral fats in the small intestine or by increasing excretion of fats as feces through adhesion to the consumed fat. However, the above mechanism has a problem of distended stomach, uncomfortable expulsion of gas, fat in feces.

Second mechanism regulates the body fat by accelerating oxidation of fat taken from foods or body fat accumulated in the body. Enzymic activity that involves in fatty acid oxidation is increased, thereby accelerating fatty acids to be transported to mitochondria. As a result, beta oxidation within mitochondria is stimulated, and eventually, the energy production from fat is increased.

The third mechanism inhibits synthesis of fatty acid from acetyl CoA by reducing the activity of the enzyme relates to fat synthesis such as fatty acid synthase and citrate lyase, etc.

Especially, the combustion process producing energy and heat by directly breaking down the accumulated fat or by oxidizing fat is important for energy consumption of the body, where numerous enzymes and genes are involved in. Hormone sensitive lipase is the most important enzyme in the step of decomposing neutral fats in adipose tissues, and in order for the fatty acids to be degraded and used as energy, they should be transported to mitochondria where energy is produced. The fatty acids (acyl CoA) activated in the cytoplasm should pass through the membranes (outer and inner membranes) of mitochondria to be transported inside mitochondria. This process is catalyzed by an enzyme called carnitine palmitoyltransferase (CPT) which exists as CPTI or CPTII. In addition, acyl-CoA oxidase, which is an enzyme in peroxisome, produces trans-2,3-dehydroacyl-CoA and $H_2O_2$ from acyl CoA and $O_2$, and is a rate-limiting enzyme which acts at the very first step of β-oxidation of fatty acid. Uncoupling protein (UCP) of mitochondria is found in brown fat, white fat, and muscle cells. UCP uncouples the oxidative phosphorylation process in mitochondria of the subject cell thereby reducing ATP production and generating heat. Therefore, it is reported that the expression degree of UCP is relevant to obesity since it influences the energy consumption. Further, AMPK is reported to play a key role in oxidation of fat.

Phosphorylation of ACC according to activation of AMPK is important for the reduction of body fat by the mechanism of increasing fatty acid oxidation. Therefore, if ACC enzyme activity is regulated by AMPK at the initial stage of fatty acid synthesis, the accumulation of unnecessary fat in the body can be inhibited, thereby resulting in inhibition of weight gain. Furthermore, during one of the important regulation mechanisms of AMPK, the activity of HMG-CoA reductase (a target molecule of statin, which is a therapeutic agent for hyperlipidemia) is also inhibited. This indicates that cholesterol synthesis can be also regulated in hepatic tissue by AMPK activation, and thus, the effect of reducing the level of neutral fat and cholesterol in the blood can be also achieved. Therefore, if AMPK is activated, the synthesis of fat is reduced as well as the oxidation is increased thereby increasing oxidation of body fat, which results in weight loss due to decrease in body fat as well as decrease in level of neutral fat and cholesterol in the blood.

Muscle occupies the largest portion of the body, and securing optimum muscle mass is necessarily required to maintain body function and to prevent metabolic disease. It is known that, generally, about 24% of the population aged 65-70 is experiencing muscle atrophy due to aging, and about 20% is having difficulties due to loss of myofunction. As reduction in physical activity, dysfunction, cancer, obesity, type 2 diabetes, and aging, etc. progress, muscle mass and motor ability decrease, and thus the quality of life is remarkably declined. Particularly, as Korea is rapidly becoming an aging society along with rapid economic growth, development in healthcare technology and improvement in nourishment, an interest in the treatment of the diseases relate to muscle wasting such as muscle atrophy is growing.

Muscle size is regulated by the intracellular signaling pathways inducing anabolism or catabolism which occur in the muscle. When the signaling reaction, which induces the synthesis of muscle protein, increases, the synthesis of muscle protein increases thereby leading to hypertrophy where the muscle grows in size or increase in the number of muscle fibers (hyperplasia) (The Korea Journal of Sports Science, 20(3): 1551-1561, 2011).

The factors that involve in the synthesis of muscle protein induce the protein synthesis by phosphorylating downstream proteins upon stimulation of phosphatidylinositol-3 kinase (PI3K)/Akt pathway within muscle cells. The activity of mammalian target of rapamycin (mTOR) by PI3K/Akt signaling is recognized as a key growth signaling factor which integrates various growth signals in the cell. mTOR contributes to increase of muscle mass by inducing muscle protein synthesis through activation of the two factors that initiate mRNA translation, i.e., 4E-binding protein (4EBP1) and phosphorylated 70-kDa ribosomal S6 kinase (p70S6K) (The Korea Journal of Sports Science, 20(3): 1551-1561, 2011; The International Journal of Biochemistry and Cell Biology, 43(9): 1267-1276, 2011). On the contrary, when forhead box (FoxO), which is a transcription factor, moves inside a nucleus from cytoplasm, it increases the expression of MuRF-1 and atrogin-1, which are a E3 ubiquitin ligase factor involves in proteolysis (Disease Models and Mechanisms, 6: 25-39, 2013). If their expression level increases, proteolysis in muscle is accelerated, and thus, muscle mass is decreased. Therefore, acceleration of mTOR activation and inhibition of atrogin-1 and MuRF-1 expression lead to an increased amount of muscle protein, and result in muscle mass increase.

In the present specification, 'capacity of exercise performance' or 'motor ability' is defined as a degree of performing physical motions rapidly, strongly, accurately, for a long time, proficiently, wherein the motions are observed in daily life or sports, which are externally categorized as running, jumping, throwing, swimming, etc. Exercise performance is evaluated by the factors such as muscular strength, agility, and physical endurance, etc. The term 'improvement of capacity of exercise performance' meant to improve or enhance the capacity of exercise performance.

Physical health can be maintained through exercise, and the result of exercise will be different depending on the individual capacity of exercise performance. If muscle is lost due to congenital physical disabilities or acquired reasons such as hospitalized for a long time, etc., muscular strength decreases, and exercise performance also weakens. To solve above problem, various studies on the substances having exercise mimetic effect are conducted. After the fact that resveratrol extracted from the grape-skin remarkably increases capacity of exercise performance has been reported (Nature 444:337-342, Cell 127: 1109-1122, Exp Mol Med 39:222-229), a subsequent study reported that intraperitoneal injection of 5-aminoimidazole-4-carboxamide ribonucleotide (AICAR), which is a peroxisome proliferator-activated receptor δ (PPAR δ) agonist, along with a 4-week training exercise increased the distance of exercise performance by 44% without training. This has opened up possibilities that the alternative substance for exercise can be formulated into pharmaceuticals. Korean mistletoe extract was reported to increase the activity of mitochondria in muscle cells and increase the distance of exercise performance by 150% in the mouse treadmill test (Korean J. Food Nurt. Vol. 29. No. 4, 505~512, 2016).

In case of an exercise that requires maximum power in a short-term, the main pathway providing ATP is the process that phosphocreatine is degraded into creatine by creatine kinase, where ATP is regenerated by transferring phosphoryl group of phosphocreatine to ADP. This contributes to a generation of large amount of ATP within 5-10 seconds. Further, another process is the degradation of glycogen to lactate during glycolysis or glycogenolysis. This contributes mostly to a rapid ATP generation within about 2 minutes. The shorter the exercise time, the higher the relative contribution to ATP generation gets. During a sprint, phosphocreatine runs low, glycogenolysis is activated, and the degradation rate of ATP often exceeds the synthesis rate of ATP. This results in excessive degradation of ATPs and increase in the amount of the final products (ADP, AMP, IMP, ammonia, etc.) of the degradation of intercellular adenine nucleotides. A few of the produced inosine phosphate (IMP) is converted to inosine or hypoxanthine, and effused to venous blood of muscles. If the level of H+ isolated from lactic acid, which is excessively produced from glycolysis and glycogenolysis, exceeds the capacity that can be removed by the body buffer system along with accumulation of ADP and phosphate produced by degradation of adenine nucleotide in the cell, pH is lowered, and this relates to the fatigue during a short-term maximal exercise.

Fatty acids in muscle cells are resynthesized with glycerol, and then stored again within the muscle in a form of neutral fat or synthesized with protein in the muscle and used when mitochondria generate energy. A peroxisome proliferator-activated receptor gamma coactivator-1α (PGC-1α) is activated in cell nucleus upon AMPK activation thereby exerting an effect of increasing motor ability.

The inventors of the present invention confirmed that the *Gynostemma Pentaphyllum* leaves extracts of the present invention has superior effect of inhibiting adipocyte differentiation and activating AMPK, and thus shows prevention or treatment effect of obesity. Further, the extract is confirmed to be effective for improving the capacity of exercise performance and preventing or treating muscle loss by accelerating muscle cell differentiation and glucose uptake, and inhibiting the proteins which break down muscles.

Further, AMPK forms heterotrimeric complex with a single catalytic α subunit (α1 or α2), two regulatory subunit β (β1 or β2), and γ (γ1, γ2 or γ3) of serine/threonine kinase. The differences between each subunit in terms of the distribution in tissues and degree of expression are as follows. Catalytic α1 subunit is mostly distributed in the tissues of kidney, lung, and adipose, whereas catalytic α2 subunit is predominantly distributed in a heart, muscle, and liver. Regulatory β1 subunit is mostly distributed in liver, while β2 subunit is distributed in muscles. Regulatory γ1 and γ2 subunits are widely distributed in the tissues; however, most of γ3 is particularly distributed in the muscles. An action of AMPK is an important sensor that detects energy level within the cell, and the result therefrom plays a key role in controlling appetite and weight, glycemic control, and blood lipid metabolism control, etc. AMPK activation is occurred by binding of AMP to γ-subunit of AMPK due to the AMP level increased by the ATP consumption which is shown because of intensive training or long-term starvation. Substantial activation is shown through the phosphorylation of threonine (Thr)-172 residue of AMPK a subunit by LKB1 or CaMKK, a super ordinate phosphorylation enzyme.

Phosphorylated AMPK inhibits the synthesis of fatty acid and cholesterol, which is a biochemical reaction that consumes ATP, and on the other hand, activates glycolysis and β-oxidation of fatty acids where ATP is generated. Moreover, the phosphorylated AMPK increases the amount of glucose transporter 4 (GLUT4), which is the absorption passage for glucose in the cell membrane. Meanwhile, AMPK activation increases cell membrane transport of GLUT4, which is the intracellular absorption passage of glucose, regardless of PI3K signaling mechanism according to the actions of insulin. Further, when AMPK is activated by phosphorylation, hydroxymethylglutaryl (HMG)-CoA reductase is phosphorylated, which is another downstream protein of a key enzyme of synthesis of cholesterol. As a result, HMG-CoA reductase is inactivated, and thus the synthesis of cholesterol is inhibited thereby declining the cholesterol level in the blood.

As to the regulation of AMPK in the muscle, contraction and hypoxia show similar effect in the skeletal muscles compared to insulin. ATP consumption in the muscles is increased by muscular contraction by exercise. AMPK activation is induced by the rate of change of AMP/ATP and creatine/phosphocreatine, and degree of activation is proportional to the intensity of exercise. The activation of muscular contraction rapidly inhibits ATP-consuming mechanism, and also activates carbohydrate and fatty acids that store ATP in the muscle. AMP binds to the two CBS domains of γ-subunit, and activates phosphorylation of Thr172 in α-subunit directly through allosteric activation and indirectly through the mechanism of assisting the binding of AMPK to other kinases. Binding of AMP to γ-subunit is inhibited by the ratio of ATP and ATP/AMP free, and thus, the reduction of the ratio is the most important factor that activates AMPK during the contraction of the muscle cell contracts and exercise. The mechanism of increasing glucose uptake regarding muscular contraction is clearly different from the mechanism of increasing glucose uptake by insulin stimulation. Increase in $Ca^{2+}$ in the cell causes contraction, and this leads to an increase in glucose uptake. In this regard, it was clarified that if a gene called AMPK is activated, physical strength of experimental mouse is improved due to muscle development without any exercises; and if a PPAR delta gene is activated, the mouse can run longer distance for longer time. Therefore, muscle loss can be prevented by activating the genes such as AMPK and PPAR delta.

Saponin compounds included in *Gynostemma Pentaphyllum* leaves contain saccharide. Between the saponin compounds, there exists saponin that can be absorbed in the body in a form of glycoside. On the other hand, most of the saponins that are difficult to be absorbed are converted into an effective saponin that can be absorbed in a small molecular form by breaking its bonds with glycoside, but some are not converted to such a form. In view of the above, as to red ginseng that contains saponin similar to that of *Gynostemma Pentaphyllum* leaves, it was reported that its bioavailability is increased by converting the large molecular saponin component into a small molecular form (Korean Patent No.

10-1200571). Therefore, converting gypenoside glycoside of *Gynostemma Pentaphyllum* leaves into effective and absorbable gypenoside (non-glycoside or small molecular saponin with only a few substitutions by saccharides) is a very significant factor for increasing bioavailability and efficacy.

The present invention provides a preparation method of *Gynostemma Pentaphyllus* leaves extracts to provide an extract with increased amount of the small molecular effective saponin such as ginsenoside Rg3, gypenoside L, gypenoside LI, etc. as well as particularly decreased amount of benzopyrene comprising the following steps: (1) drying fresh *Gynostemma Pentaphyllus* leaves after roasting or steaming; (2) treating the dried *Gynostemma Pentaphyllus* leaves with steam; (3) adding water of 1 to 100-fold volume and then manufacturing a hot water extract by carrying out hot water extraction at 100-150° C., 0.5-10 atm for 1-120 hours; (4) adding $C_1$-$C_4$ lower alcohol of 1 to 100-fold volume to the residual from the hot water extraction and then preparing an alcohol extract of residual from the hot water extraction by carrying out alcohol extraction at 50-100° C. for 1-120 hours; and (5) mixing the hot water extract of step (3) and the alcohol extract of step (4), and then filtering and concentrating the mixture.

High temperature roasting, which is often used to prepare *Gynostemma Pentaphyllus* leaves extracts, results in conversion of various precursors included in *Gynostemma Pentaphyllus* leaves such as ginsenoside, gypenoside, etc. to the precursors which are converted to small molecular effective saponin such as Rg3, gypenoside L, gypenoside LI, etc. However, the components such as protein, carbohydrate, lipid, etc., which are contained in *Gynostemma Pentaphyllus* leaves together with saponin, are converted and generate large amount of benzopyrene, and raise safety issue. On the other hand, when *Gynostemma Pentaphyllus* leaves are naturally dried, conversion of precursors to small molecular effective saponin barely takes place, and thus the efficacy of *Gynostemma Pentaphyllus* leaves extracts becomes a problem.

Figure 13:
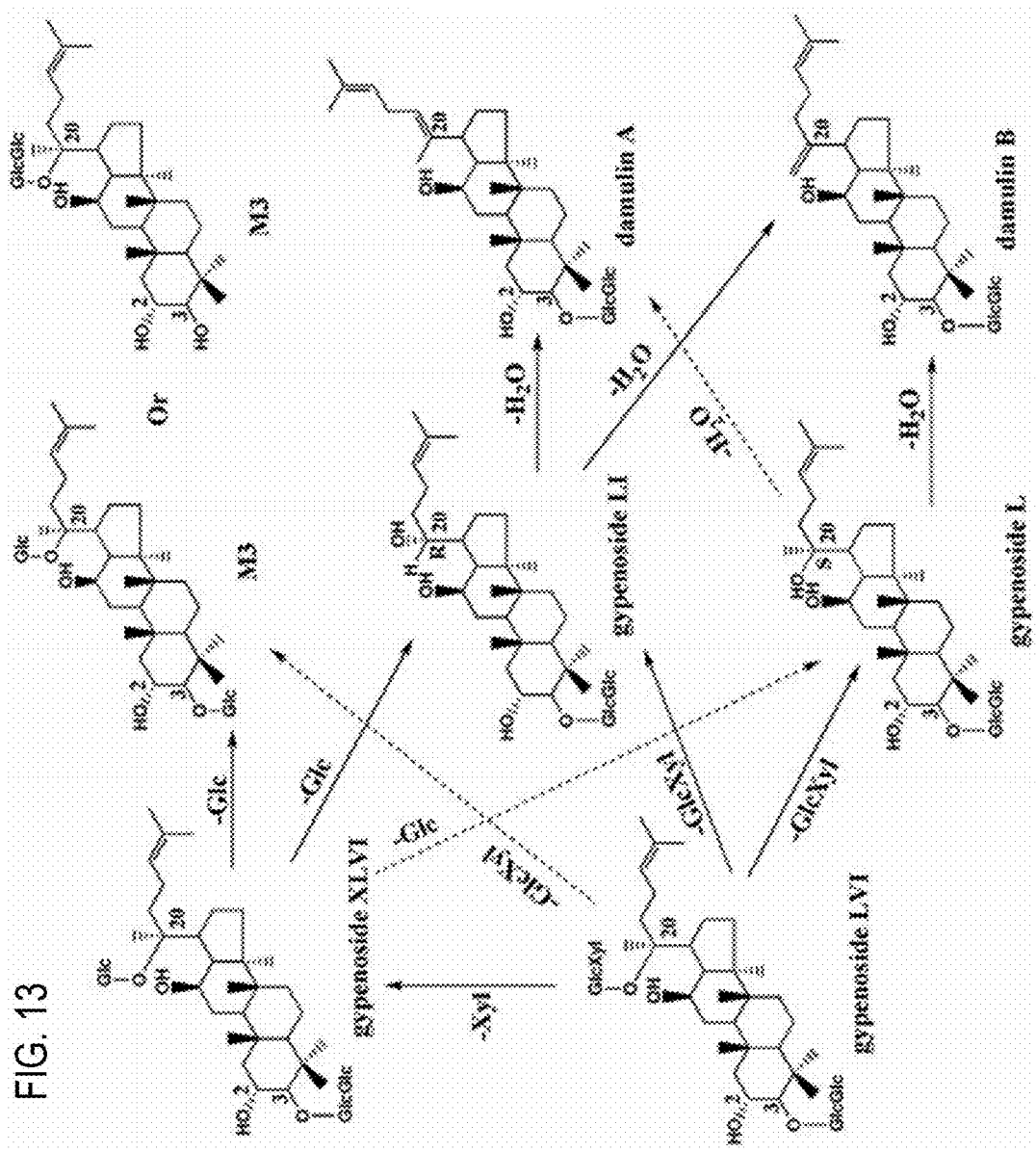
FIG. 13 shows the relationship between the saponin precursor and small molecular saponin components.
Figure 14:
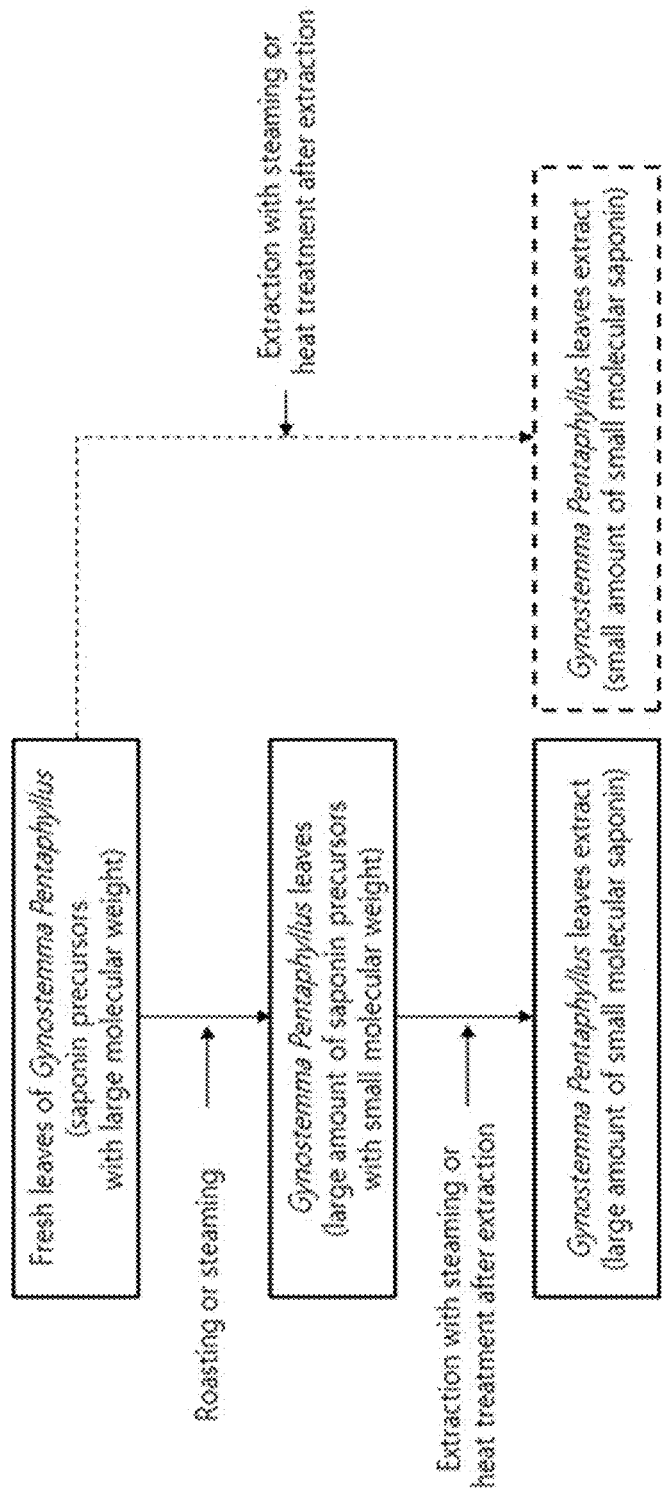
FIG. 14 shows that in the present invention, the heat treatment should be conducted to the fresh leaves of Gynostemma Pentaphyllus to maximize the amount of small molecular active ingredients.

In this regard, the inventors of the present invention found out that the heat treatment should be conducted to the fresh leaves of *Gynostemma Pentaphyllus* to maximize the amount of small molecular active ingredients. The present inventors assumed based on the relationship between the below saponin precursor and small molecular saponin components (Chen et al., J. Chromatogr. B Analyt Technol Biomed life Sci, 969: pp. 42-52; shown in FIG. 13) that if the fresh leaves are roasted or steamed, the saponin precursors with large molecular weight are converted to the saponin precursors with small molecular weight, and then they are converted to small molecular effective saponin when extracted at the high temperature.

The step of treating fresh leaves with heat is roasting or steaming, and generally, drying is performed together after steaming. Generally, roasting is to heat the fresh leaves in an open container at a certain or higher temperature, and steaming is conducted at the similar temperature to roasting, but applies heat in a sealed container. These processes are routinely conducted to sterilize harmful germs, prevent deterioration, and enhance fragrance and flavor. Generally, *Gynostemma Pentaphyllus* leaves are roasted at the high temperature of 250-500° C., in a traditionally method, tea leaves are placed in a hot kiln or pot and mixed by stirring with hands. Such a method results in the low conversion rate of active ingredient precursors to active ingredients or excessive generation of benzopyrene due to the inconsistent conversion ratio of active ingredient precursors to active ingredients. Until now, no study was conducted on how the roasting or steaming process of *Gynostemma Pentaphyllus* leaves influence the product quality of *Gynostemma Pentaphyllus* leaves.

The present invention found out that the amount of benzopyrene tends to simultaneously increase with the amount of effective saponin according to the process of roasting or steaming, drying, extracting, and heat treatment of *Gynostemma Pentaphyllus* leaves and tried to solve the safety problem and efficacy. As a result, the present invention was completed by confirming that if *Gynostemma Pentaphyllus* leaves are extracted by the roasting or steaming, treatment of steam and hot water extraction according to the present invention, the amount of protein, carbohydrate, and lipid components in *Gynostemma Pentaphyllus* leaves converted to benzopyrene decrease and the amount of small molecular effective saponin such as Rg3, gypenoside L, gypenoside LI, etc. increases.

First, in step (1) fresh leaves of *Gynostemma Pentaphyllus* are roasted or steamed, and then dried.

Dried *Gynostemma Pentaphyllus* leaves can be prepared by drying after roasting or steaming fresh leaves of *Gynostemma Pentaphyllus* at 90-180° C., preferably, at 110-150° C., for 1 to 100 hours using electric heater. An electric heater is a device of which the temperature can be controlled, such as steam heat exchange system or a container equipped with steam jacket, etc. Roasting or steaming and then drying fresh *Gynostemma Pentaphyllus* leaves at the above temperature and time range using electric heater is preferable for the large-scale manufacturing process since a large amount of *Gynostemma Pentaphyllus* leaves can be uniformly heated while declining the generation of benzopyrene. Since the precursors of the active ingredients of *Gynostemma Pentaphyllus* leaves are predominantly glycosides, in principle, it was expected that at the high temperature, the amount of the active ingredients could be increased by breaking the bonds of saccharides or lipids contained in *Gynostemma Pentaphyllus* leaves. However, increase in benzopyrene generation was accompanied. Nonetheless, it is advantageous to roast or steam and then dry *Gynostemma Pentaphyllus* leaves by an electric heater that can control temperature under the condition designated by the present invention since the amount of the active ingredients are increased while generation of benzopyrene is declined through properly controlling the temperature.

Next, the dried *Gynostemma Pentaphyllus* leaves are treated with steam in step (2).

The steam treatment can be carried out at 100-130° C. for 0.5-10 hours. It is preferable to treat *Gynostemma Pentaphyllus* leaves with steam before the extraction as a preprocessing step since the amount of benzopyrene contained in *Gynostemma Pentaphyllus* leaves extracts will be remarkably decreased.

Meanwhile, after completing step (1) and step (2) above, the process of drying the above steam-treated *Gynostemma Pentaphyllus* leaves once again and treating them with steam can be added/repeated for 1-5 times.

The process of drying and treating the *Gynostemma Pentaphyllus* leaves with steam after roasting or steaming can be carried out as follows: The above *Gynostemma Pentaphyllus* leaves are roasted or steamed, and dried at 90-180° C., preferably at 110-150° C., for 120 hours, and then treated with steam at 100-130° C. for 10 hours. It is preferable to perform the above process 2 to 4 times. Particularly, it is confirmed from the working examples of the present invention that when the process of roasting or steaming, drying, and then treating with steam is repeatedly carried out, the amount of small molecular effective saponin in the *Gynostemma Pentaphyllus* leaves, which are mainly ginsenoside Rg3, gypenoside L, gypenoside LI, etc., increases while the amount of benzopyrene more decreases. Meanwhile, if the process of roasting or steaming, drying, and then treating with steam is not conducted under the preferable temperature and time range indicated in the present invention, the superior effect as in the present invention is difficult to obtain.

Subsequently, in step (3), a hot water extract is prepared by adding water of 1 to 100-fold volume to the steam-treated *Gynostemma Pentaphyllus* leaves and then carrying out hot water extraction at 100-150° C., 0.5-10 atm for 1-120 hours.

When preparing the above hot water extract, preferably, pH can be regulated from 0 to 7, and more preferably from pH 3 to 5. The conversion rate to active ingredients can be increased by regulating pH within the preferable range of the present invention.

The acids used when regulating pH can be citric acid, butyric acid, hydrochloric acid, trifluoroacetic acid, treichloroacetic acid, acetic acid, vitamin C, malic acid, lactic acid, succinic acid, alginate, etc. Further, the acids that can lower pH can be used and can be one or more selected from the above.

The heating temperature when preparing the above hot water extract can be 100-150° C., preferably 110-130° C., most preferably 115-125° C. Further, if the heating temperature is below the above range, the extraction yield decreases or the conversion rate of precursors of the active ingredients to the active ingredients may decrease; and if the heating temperature exceeds the above range, it is not preferable since the active ingredients can be destroyed.

In addition, if the heating time is shorter than the above range, the extraction yield of the active ingredients may decline.

Next, step (4) prepares an alcohol extract by adding $C_1$-$C_4$ lower alcohol of 1 to 50-fold volume to the residual remained after the hot water extraction and then carrying out an alcohol extraction at 50-100° C. for 1-120 hours to extract to the maximum the aqueous and lipid-soluble components contained in the residual of the hot water extract of *Gynostemma Pentaphyllus* leaves.

The lower $C_1$-$C_4$ alcohol can be one or more selected from methanol, ethanol, propanol, isopropanol, and butanol.

The lower alcohol is preferably 20-90% (v/v), more preferably 40-70% (v/v), of alcohol aqueous solution.

The heating temperature when preparing the alcohol extraction is 50-100° C., preferably 70-90° C. If the heating temperature is below the above range, the extraction yield may decrease; and if it exceeds the above range, it is not preferable since problems during process may occur due to solvent vapor.

In addition, if the heating time is shorter than the above range, the extraction yield of the active ingredients may decrease.

Next, in step (5), the hot water extract of step (3) and the alcohol extract of step (4) are mixed, filtered, and then concentrated.

The mixture ratio of the hot water extract of step (3) and the alcohol extract of step (4) is preferably 1:0.5-2 in volume.

Further, the contaminants of the mixture of the *Gynostemma Pentaphyllus* leaves can be removed by using a general filtering method or device. For example, an extract from which the contaminants are removed can be obtained by using centrifugation or microfiltration where the size of micro filter is 0.3-0.8 μm.

The above filtered *Gynostemma Pentaphyllus* leaves extracts can be concentrated so that the solid content reaches 10-85% and then used. Further, the above *Gynostemma Pentaphyllus* leaves extracts can be prepared in a form of dried powder which went through additional process such as distillation under reduced pressure, lyophilization, or spray drying, etc.

According to the above-described method, *Gynostemma Pentaphyllus* leaves extracts which comprises 0.01-7 mg/g of ginsenoside Rg3, 1.5-70 mg/g gypenoside L, 1.5-70 mg/g gypenoside LI, and other small molecular effective saponin, and/or 10 or less ppb benzopyrene (for example, in the range from 0.01 to 10 ppb) can be provided.

Further, the *Gynostemma Pentaphyllus* leaves extracts of the present invention can comprise 0.01-7 mg/g of ginsenoside Rg3, 1.5-70 mg/g gypenoside L, 1.5-70 mg/g gypenoside LI, other small molecular effective saponin, and/or 10 or less ppb benzopyrene (for example, in the range from 0.01 to 10 ppb). In particular, the *Gynostemma Pentaphyllus* leaves extracts of the present invention may have above features in a form of dried powder.

Specifically, the *Gynostemma Pentaphyllus* leaves extracts of the present invention may comprise 0.01-7 mg/g of ginsenoside Rg3, 1.5-70 mg/g gypenoside L, 1.5-70 mg/g gypenoside LI, other small molecular effective saponin; may additionally comprise 10 or less ppb benzopyrene (for example, in the range from 0.01 to 10 ppb); and may exist in a form of dried powder.

In addition, the *Gynostemma Pentaphyllus* leaves extracts of the present invention may comprise 10 or less ppb benzopyrene (for example, in the range from 0.01 to 10 ppb); may additionally comprise 0.01-7 mg/g of ginsenoside Rg3, 1.5-70 mg/g gypenoside L, 1.5-70 mg/g gypenoside LI, other small molecular effective saponin; and may exist in a form of dried powder.

The *Gynostemma Pentaphyllus* leaves extracts of the present invention has lower toxicity since the amount of benzopyrene is low, and has excellent effect in preventing, improving, or treating diabetes or obesity, muscle loss, or enhancing motor ability due to increase in the amount of small molecular effective saponin such as Rg3, gypenoside L, gypenoside LI, etc.

The present invention further provides a composition comprising the *Gynostemma Pentaphyllus* leaves extract of the present invention as an active ingredient. Particularly, the composition of the present invention can be used for the prevention, improvement, or treatment of obesity or diabetes, muscle loss, and also for enhancing the capability of exercise performance. Depending on its method of use and purpose, the composition of the present invention can be a pharmaceutical composition, a composition for food, a composition for health care food, a composition for quasi-drug, etc., however not limited thereto.

Specifically, the pharmaceutical composition of the present invention comprises the *Gynostemma Pentaphyllus* leaves extract as an active ingredient, and may further comprise a pharmaceutically acceptable carrier. The pharmaceutically acceptable carrier is routinely used for drug formulation, and includes saline solution, sterile water, buffered saline solution, cyclodextrin, dextrose solution, maltodextrin solution, glycerol, ethanol, liposome, etc.; however, it is not limited thereto and may further comprise other commonly used additives such as antioxidant, buffer, etc. as required. Further, it can be preferably formulated as a solution, emulsion, fluid, and formulation depending on each component that is comprised by adding diluent, dispersant, surfactant, lubricant, etc. There is no limitation for the formulation of the pharmaceutical composition of the present invention; however, it can be formulated as an injection, orally administered preparation, dermal preparation for external use, etc.

The pharmaceutical composition can be orally or parentally administered (for instance, intravenously, subcutaneously, intraperitoneally, or topically applied) and the dosage may differ depending on the condition and weight of the patient, severity of disease, drug form, administration route and time, however, can be properly selected by a person skilled in the art.

Further, the dose level selected for the above composition will be determined based on the activity of the compound, administration route, severity of condition to be treated, condition or past medical history of patient to be treated. However, starting from a dose lower than the level required to obtain a desired treatment effect, and slowly increasing the dose until the desired effect is achieved is within the knowledge of the art, and a preferable dose can be determined according to the age, gender, body type, body weight. The composition can be additionally processed prior to be formulated into a pharmaceutically acceptable pharmaceutical formulation, and preferably can be pulverized or polished to smaller particles. Further, the composition can be determined uncreatively, while may vary depending on the condition and patient to be treated. For a preferable effect, the effective dose of the *Gynostemma Pentaphyllus* leaves extracts of the present invention is 0.001-400 mg/kg, preferably 0.01-100 mg/kg, and can be administered once, twice, or three times per day. The dose above does not limit the scope of the present invention in any way.

The pharmaceutical composition of the present invention can be prepared as a unit dosage form formulated by using a pharmaceutically acceptable carrier and/or excipient or prepared by placing into a multi-dose container, according to the method that a person skilled in the art can easily practice. The formulation can be any form suitable for pharmaceutical formulation such as oral formulation (powder, granule, tablet, capsule, suspension, emulsion, syrup, aerosol, etc.), preparation for external use (ointment, crème, etc.), and sterilized solution for injection, etc., and can additionally comprise dispersant or stabilizer.

In addition, the present invention provides a composition for food preventing or improving obesity or diabetes, muscle loss comprising *Gynostemma Pentaphyllus* leaves extracts as an active ingredient. The composition for food of the present invention includes every form such as functional food, health functional food, nutritional supplement, health food, and food additives, etc. The composition for food of above types can be prepared in various forms according to the common methods known in the relevant art.

According to the present invention, the amount of the *Gynostemma Pentaphyllus* leaves extracts can be 0.001-80% (w/w), preferably 0.05-50% (w/w), of the total weight of the whole composition for food. If the amount of *Gynostemma Pentaphyllus* leaves extracts is lower than the above range, it is difficult to expect the effect of *Gynostemma Pentaphyllus* leaves extracts.

As the specific examples for the above composition for food, the *Gynostemma Pentaphyllus* leaves extracts of the present invention can be manufactured and drunk as tea, juice, or drinks, etc. or formulated as granules, capsule, or powder and taken in a form of health functional food. Further, *Gynostemma Pentaphyllus* leaves extracts of the present invention can be mixed and prepared as a composition with the publicly known substance or active ingredient that is known as to have anti-obesity effect or anti-diabetes effect, inhibitory effect on muscle loss. For example, besides *Gynostemma Pentaphyllus* leaves extracts, the composition for food of the present invention can additionally contain small amount of mineral, vitamin, saccharides, and publicly known ingredients having anti-obesity activity or anti-diabetes activity, inhibitory effect on muscle loss, etc.

In addition, the examples of the composition for food can be drinks, meat, sausage, bread, biscuit, rice cake, chocolate, candy, snake, pizza, ramen, other noodles, gums, dairy products including ice-creams, various types of soups, etc., and include all of the functional foods within the common definition.

Further, the health functional food composition is characterized in comprising one or more from carrier, diluent, excipient, and additive, and formulated as one selected from tablet, pill, granule, powder, capsule, and liquid formulation.

The *Gynostemma Pentaphyllus* leaves extracts of the present invention can be added to the food as is or used together with other food or food ingredients, and can be used properly according to the common method. The mixed amount of active ingredient can be determined depending on its use (for prevention or improvement). Generally, the amount of the composition for food that can be added to the food is 0.01-100% (w/w) of the total weight of the food. However, when taking in the composition for food for prevention or improvement of obesity or for a long-term intake for the purpose of health care, the amount can be below the above range, and the active ingredient can also be used in the range above since it has no safety problem.

Hereinafter, *Gynostemma Pentaphyllum* leaves extracts according to the present invention will be described in detail in reference to the working examples.

EXAMPLES

Example 1

Method of Roasting

To determine the active ingredient content and the amount of generated benzopyrene after roasting, 100 g of fresh *Gynostemma pentaphyllum* leaves were roasted and dried by each roasting method for 2 hours. In natural drying, thinly spread *Gynostemma pentaphyllum* leaves were dried in a shade at a windy location, and in roasting by wood fire, *Gynostemma pentaphyllum* leaves were placed into a pot heated by wood fire and stirred with hands in gloves. Roasting by gas stove fire was conducted by the same method as the wood fire roasting while adjusting the fire to a medium flame, and roasting by electric heater was performed in a rotating cylinder at 135° C. Each roasting was naturally dried after checking that the surfaces of the *Gynostemma pentaphyllum* leaves were dried. Next, 1 L of water was added after a steam treatment at 121° C., soaked for an hour, extracted at 121° C., 1.2 atm for 4 hours, and a supernatant was collected. To the residual, 1 L of 50% (v/v) ethanol aqueous solution was added and extracted at 90° C. for 3 hours. The supernatant was mixed with the water extract and filtered, and then concentrated under reduced pressure. It was then lyophilized, and thus *Gynostemma pentaphyllum* leaves extracts was prepared. Benzopyrene in the extract was analyzed by the HPLC method recommended by the Korean Ministry of Food and Drug Safety. The HPLC analysis conditions of the active ingredient are shown in Table 1 below, and the analyzed results are shown in Table 2 below.

TABLE 1

| Detector | DAD or PDA (204 nm) |
| --- | --- |
| Column | ZORBAX Eclipse Plus C18 |
| Flow rate | 1.0 mL/min |
| Injection volume | 10 μL |

| | Solvent A: DW, Solvent B: Acetonitrile | | |
| --- | --- | --- | --- |
| | Time (min) | Solvent A (%) | Solvent B (%) |
| Mobile phase | 0 | 60 | 40 |
| | 20 | 60 | 40 |
| | 35 | 50 | 50 |
| | 40 | 50 | 50 |
| | 40.1 | 0 | 100 |
| | 50 | 0 | 100 |
| | 50.1 | 60 | 40 |
| | 60 | 60 | 40 |

TABLE 2

| Component | Natural drying | Roasting by wood fire | Roasting by gas stove fire | Roasting by electric heater |
| --- | --- | --- | --- | --- |
| Benzopyrene (ppb) | 1.21 | 25.66 | 3.65 | 2.97 |
| Rg3 (mg/g) | ND | 3.47 | 3.15 | 3.38 |
| Gypenoside L (mg/g) | ND | 29.92 | 30.14 | 29.67 |
| Gypenoside LI (mg/g) | ND | 25.1 | 24.12 | 24.23 |

As Table 2 demonstrates, *Gynostemma pentaphyllum* leaves that did not undergo roasting have the lowest benzopyrene content, but almost no active ingredients were detected, and thus are not preferred. Roasting by electric heater, which results in lower benzopyrene content and increased active ingredient content compared to other roasting methods, is confirmed to be advantageous. At the same time, small amounts of Damulin A and B were also detected.

Example 2

Roasting Temperature

To determine the active ingredients content and the amount of generated benzopyrene according to the roasting temperature, 100 g of fresh *Gynostemma pentaphyllum* leaves were roasted and dried for 2 hours by adjusting the temperature of the electric heater, extracted by the extraction method and steaming process of Example 1, and underwent a concentration process. Subsequently, the benzopyrene and active ingredients content in the extract were analyzed as shown in Table 3 below.

TABLE 3

| | Temperature for Roasting (° C.) | | | | | | | |
| --- | --- | --- | --- | --- | --- | --- | --- | --- |
| Component | 50 | 70 | 90 | 120 | 150 | 180 | 220 | 300 |
| Benzopyrene (ppb) | 1.15 | 1.51 | 2.72 | 2.83 | 3.12 | 4.15 | 18.87 | 26.34 |
| Rg3 (mg/g) | 0.03 | 0.07 | 0.51 | 3.17 | 3.20 | 3.22 | 3.32 | 3.45 |
| Gypenoside L (mg/g) | 1.7 | 2.4 | 13.8 | 29.4 | 30.1 | 30.3 | 31.7 | 32.7 |
| Gypenoside L I (mg/g) | 3.5 | 5.9 | 8.7 | 23.8 | 24.1 | 23.9 | 24.5 | 24.7 |

As Table 3 demonstrates, the active ingredients content tends to increase as the roasting temperature increases, but so does the content of benzopyrene, a harmful substance. Therefore, it was confirmed that roasting at 90-180° C. is optimal.

Example 3

Comparison of Roasting and Steaming

Roasting and steaming are general methods of heat treatment to increase the active ingredients of food extracts. Roasting involves heating the *Gynostemma pentaphyllum* leaves placed in an open container at a certain/higher temperature, while steaming is conducted at a similar temperature to roasting, but in a sealed container. Therefore, to determine the active ingredients content and the amount of generated benzopyrene, 100 g of fresh *Gynostemma pentaphyllum* leaves were roasted and dried for 2 hours while adjusting the temperature of the electric heater to 135° C., and extracted by the steam treatment and extraction method of Example 1. The benzopyrene and active ingredients contents were analyzed as shown in Table 4 below.

TABLE 4

| Component | Roasting | Steaming |
| --- | --- | --- |
| Benzopyrene (ppb) | 2.84 | 3.05 |
| Rg3 (mg/g) | 3.25 | 3.41 |
| Gypenoside L (mg/g) | 28.88 | 28.17 |
| Gypenoside LI (mg/g) | 24.12 | 24.55 |

As Table 4 demonstrates, no significant differences in the active ingredients content were observed other than that roasting resulted in slightly lower benzopyrene content. Thus, roasting and steaming displayed hardly any difference as a heat treatment method for *Gynostemma pentaphyllum* leaves.

Example 4

Elimination of Benzopyrene by Steam Treatment Process

The benzopyrene contents of *Gynostemma pentaphyllum* leaves roasted by electric heater when the leaves were treated and not treated with steam were observed. The content of remaining benzopyrene in *Gynostemma pentaphyllum* leaves was measured for a case where 100 g of *Gynostemma pentaphyllum* leaves roasted and dried at 135° C. for 2 hours with an electric heater were treated with steam at 121° C. for 60 minutes, and for a case where no steam treatment was conducted. The extraction method and the method for measuring benzopyrene content in *Gynostemma pentaphyllum* leaves were the same as those in Example 1, and the results are shown in Table 5 below.

TABLE 5

|  | Steam treatment | No steam treatment |
|---|---|---|
| Benzopyrene content (ppb) | 2.91 | 5.80 |

As can be seen from Table 5 above, the benzopyrene content of the steam-treated *Gynostemma pentaphyllum* leaves was remarkably reduced.

Example 5 pH of Extraction Solvent

In order to determine the active ingredients contents and amount of generated benzopyrene according to the pH of the solvent used for extraction, 100 g of fresh *Gynostemma pentaphyllum* leaves were roasted and dried at 135° C. for 2 hours using an electric heater, and treated with steam at 121° C. for 2 hours. Next, 1 L of water with various pHs adjusted by HCl or sodium bicarbonate were added to the steam treated *Gynostemma pentaphyllum* leaves. The leaves were soaked for 1 hour, neutralized after a 4-hour extraction at 121° C., 1.2 atm, and then the supernatant was collected. 1 L of 50% (v/v) ethanol was added to the residual and extracted. The supernatant was mixed with the water extracts and filtered, after which it was concentrated under reduced pressure until the content of the solid forms reached 20-25%. It was then lyophilized, and thus *Gynostemma pentaphyllum* leaves extracts were prepared. The concentrate was measured using the same analysis method as Example 1, and the results are shown in Table 6 below.

TABLE 6

| | Hot water extracts according to pH | | | | | | | | |
|---|---|---|---|---|---|---|---|---|---|
| | pH | | | | | | | | |
| Component | 1 | 2 | 3 | 4 | 5 | 6 | 7 | 8 | 9 |
| Benzopyrene (ppb) | 2.57 | 2.71 | 2.68 | 2.91 | 2.75 | 2.81 | 2.88 | 2.81 | 2.91 |
| Rg3 (mg/g) | 1.67 | 1.88 | 3.17 | 4.09 | 3.89 | 3.21 | 2.22 | 0.94 | 0.67 |
| Gypenoside L (mg/g) | 15.9 | 18.7 | 40.9 | 41.5 | 41.2 | 29.4 | 19.6 | 18.9 | 17.6 |
| Gypenoside LI (mg/g) | 14.2 | 16.9 | 38.0 | 38.1 | 37.6 | 25.2 | 14.7 | 14.3 | 13.2 |

As can be seen from Table 6 above, the benzopyrene content was similar regardless of the pH. However, the active substances such as gypenoside L, Rg3, etc., increased until pH 4, decreased above pH 4, and showed low content at pH 9. Accordingly, it was confirmed that acidic pH, particularly, pH 3 to 5, is advantageous for the extraction solvent.

Example 6

(1) Hot water extract was prepared by adding 1 L of water to 100 g of *Gynostemma pentaphyllum* leaves roasted and dried at 135° C. for 2 hours using an electric heater, and treated with steam at 121° C. for 60 minutes; soaking it for an hour; extracting it at 121° C., 1.2 atm for 4 hours; and then collecting the supernatant.

(2) Alcohol extracts was prepared by adding 1 L of 50% (v/v) ethanol aqueous solution to 100 g of the residual (residue) remaining after conducting the hot water extraction of the above *Gynostemma pentaphyllum* leaves; extracting it at 90° C. for 3 hours; and then collecting the supernatant.

(3) The hot water extract of step (1) and the alcohol extract of step (2) were mixed and then filtered. It was then concentrated under reduced pressure to achieve solid content of 20-25%, and then lyophilized. Thereby, *Gynostemma pentaphyllum* leaves extracts were prepared.

Example 7

Example 7 was performed in an identical manner to Example 6 except for the use of the extraction solvent adjusted to pH 4.

Example 8

Example 8 was performed in an identical manner to Example 1, except that the *Gynostemma pentaphyllum* leaves were prepared after roasting and drying at 135° C. for 2 hours, further followed by conducting 3 times the steam treatment process at 121° C. for 60 minutes before conducting an alcohol extraction on the steamed *Gynostemma pentaphyllum* leaves in step (1).

COMPARATIVE EXAMPLES

Comparative Example 1

The present invention is directed to a preparation method of a *Gynostemma Pentaphyllum* leaves extract which increases saponin contents such as ginsenoside Rg3, gypenoside L, gypenoside LI, etc., while decreasing the benzopyrene content. In contrast, the preparation method of *Gynostemma Pentaphyllum* leaves extract of the previous patented invention (Korean Patent No. 10-0930580) has damulin A and B as the active ingredients of *Gynostemma Pentaphyllum* leaves extracts, and aims to increase their content. Therefore, to compare the preparation methods of *Gynostemma Pentaphyllum* leaves extracts of the present invention and the previous patented invention regarding the effect of increasing the main active ingredients content of the present invention, i.e., small molecular effective saponin such as ginsenoside Rg3, gypenoside L, gypenoside LI, etc., and the effect of decreasing the benzopyrene content, comparative examples were prepared according to the preparation method of the *Gynostemma Pentaphyllum* leaves extract of the previous patented invention (Korean Patent No. 10-0930580).

Specifically, after roasting and drying 100 g of fresh *Gynostemma Pentaphyllum* leaves with wood fire for 2 hours, 1 L of 50% ethanol was added. Following the first extraction at 90° C. for 6 hours, a first supernatant was collected.

To the residual dipped materials of *Gynostemma Pentaphyllum* leaves extracts, 1 L of 50% (v/v) ethanol was added once again, and then a second supernatant was collected through a 6-hour extraction at 90° C.

The first and second supernatants were mixed together and filtered with gauze, and the solution obtained through the filtration was concentrated under reduced pressure at 60° C. to achieve a solid content of 50%. *Gynostemma Pentaphyllum* leaves extract was prepared by lyophilizing the concentrate after heating at 121° C., 1.2 atm for an hour.

Comparative Example 2

100 g of fresh *Gynostemma Pentaphyllum* leaves were roasted and dried at 135° C. for 2 hours using an electric heater, to which 1 L of water was added, and dipped in for an hour. Next, after a 4-hour extraction at 135° C., 1.2 atm, a first supernatant was collected, and thus a first hot water extract was prepared. To the residual dipped materials of the *Gynostemma Pentaphyllum* leaves extract, 1 L of water was added once more. Subsequently, a second hot water extract was prepared by collecting the supernatant after a 4-hour extraction at 135° C., 1.2 atm. The first and second hot water extracts were mixed together and filtered using gauze, and the solution obtained through the filtration was concentrated under reduced pressure at 60° C. and lyophilized. *Gynostemma Pentaphyllum* leaves extract was thus prepared.

EXPERIMENTAL EXAMPLES

Experimental Example 1

Component Analysis

To separate the active ingredients such as Rg3, gypenoside L, and gypenoside LI, etc., 1 L of purified water was added to the *Gynostemma Pentaphyllum* leaves extracts of the working examples and the comparison examples, and then the mixture was stirred for 3 minutes. 1 L of ethyl acetate was added thereto and stirred for 14 hours. After a layer separation, the water layer, which is the lower layer, was collected and the previous steps were repeated twice. 1 L of butanol was added to the collected water layer and stirred for an hour. After the stirring, it was left to stand for an hour, and the butanol layer was collected after the layer separation. Total 3 L of butanol extract solution was obtained by repeating the above process twice. 100 g of silica gel was added to the obtained butanol extract solution, and it was concentrated under a reduced pressure and prepared as a powder.

Thus-prepared powder was loaded on a silica gel column (10×70 cm), and a mixed solution of 3.6 L of chloroform and 0.45 L of methanol 0.45 L was loaded. Next, a mixed solution of 3.5 L of chloroform and 0.5 L of methanol was loaded, and subsequently, a mixed solution of 3.42 L of chloroform and 0.57 L of methanol and a mixed solution of 3.35 L of chloroform and 0.67 L methanol were loaded. As a result, total 12 fractions were obtained. Among those, $9^{th}$ to $11^{th}$ fractions, which have the highest AMPK phosphorylation activity, were concentrated. The concentration was then separated and subjected to a semi prep-HPLC under the conditions described in Table 1 above and thereby confirmed to be Rg3 and gypenoside L, gypenoside LI.

The results of the analysis are shown in Table 7 below.

TABLE 7

| Items | Example 6 | Example 7 | Example 8 | Comparative Example 1 | Comparative Example 2 |
|---|---|---|---|---|---|
| Yield rate of solid form (% by weight) | 27.7 | 26.9 | 27.5 | 19.6 | 15.4 |
| Benzopyrene (ppb) | 2.83 | 2.89 | 2.76 | 29.88 | 3.87 |
| Rg3 (mg/g) | 3.26 | 4.01 | 3.45 | 0.25 | 1.5 |
| Gypenoside L (mg/g) | 38.97 | 41.31 | 39.53 | 4.5 | 3.2 |
| Gypenoside LI (mg/g) | 38.02 | 39.65 | 38.33 | 3.1 | 1.5 |

As confirmed from Table 7 above, the benzopyrene content of the *Gynostemma Pentaphyllum* leaves extract was markedly decreased as compared to the comparative examples, and its contents of Rg3, gypenoside L, gypenoside LI was confirmed to be highly increased. In addition, small amounts of Damulin A and B were detected. In particular, Comparative example 1, which corresponds to the *Gynostemma Pentaphyllum* leaves extract prepared by the previous patented invention, turned out to be inefficient for extracting the desired active ingredients of the present patent, since its benzopyrene content is as high as about 3 to 10 times that of the present invention, whereas the amount of Rg3, gypenoside L, and gypenoside LI, which are the main active ingredients of the present patent, are only present at 1/8 to 1/12 levels of the present patent.

Experimental Example 2

Measurement of Cell Viability Using MTT

To determine whether the *Gynostemma Pentaphyllum* leaves extract obtained in the above working examples or comparative examples is toxic to the survival of the adipocytes, an experiment was conducted using an MTT (3-(4,5-dimethylthiazol-2-yl)-2,5-diphenyl tetrazolium bromide) assay. MTT assay uses the ability of the mitochondria to reduce soluble yellow medium MTT tetrazolium to insoluble purple MTT formazan.

First, 3T3-L1 preadipocyte cells were inoculated on a 24 well plate in $5 \times 10^4$ cell/mL density and cultured at 37° C. with 5% $CO_2$. After 24 hours, each concentration of *Gynostemma Pentaphyllum* leaves extracts obtained from the above working examples and comparative examples was added and cultured for additional 24 hours. After treating it with 2 mg/mL MTT and reacting for 4 hours, the medium was eliminated and dissolved with DMSO. The absorbance was measured at 570 nm using ELISA reader. The rate of cell viability is calculated with Equation 1 below, and the results are shown in FIG. 2.

Rate of cell viability (%)=(Absorbance of the tested sample/Absorbance of control group)×100　　[Equation 1]

Figure 1:
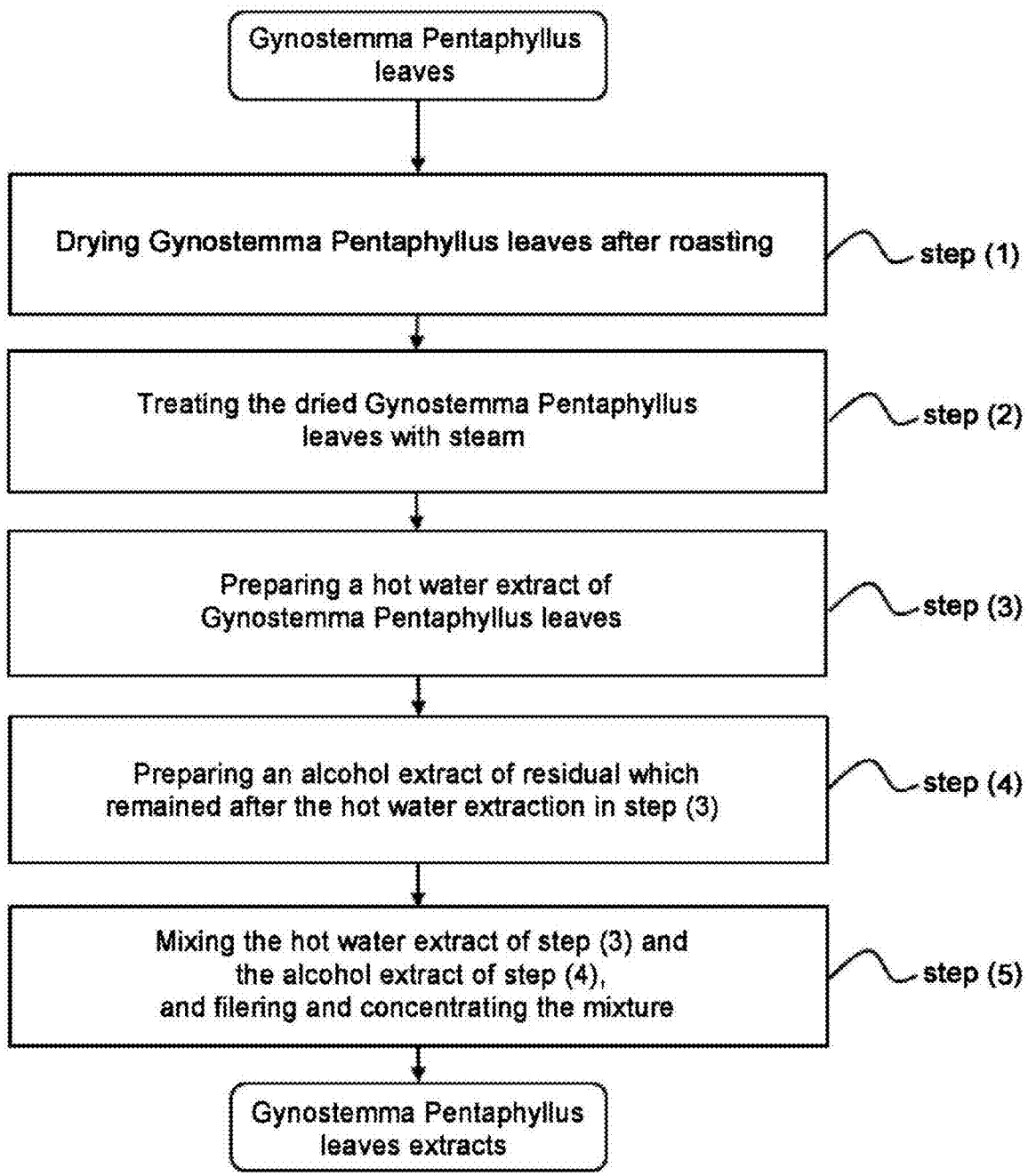
FIG. 1 shows the process chart showing the preparation method of Gynostemma Pentaphyllus leaves extract according to one embodiment of the present invention.
Figure 2:
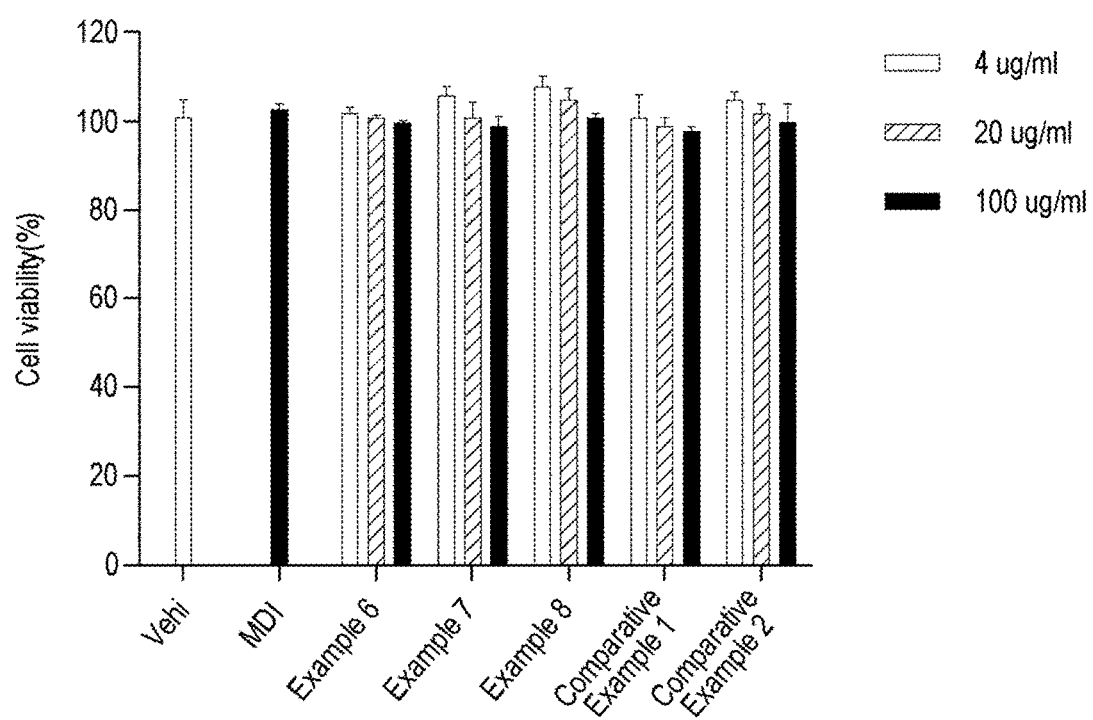
FIG. 2 is a graph showing the influence of Gynostemma Pentaphyllus leaves extract according to the working examples and comparative examples of the present invention on the cell viability.

As shown in FIG. 2, measurement results of the cell viability—after treating each concentration of *Gynostemma Pentaphyllum* leaves extract of the present invention on 3T3-L1 preadipocytes—detected no toxicity until 100 μg/mL concentration compared to the control group.

Experimental Example 3

Confirmation of Inhibition of Differentiation to Adipocytes

Experimental Example 3-1

Adipocyte Differentiation

To confirm the inhibitive activity on the proliferation of preadipocytes and adipocytes, 3T3-L1 preadipocytes were obtained from American Type Culture Collection (ATCC, Manassas, Va., USA). 3T3-L1 preadipocyte is a cell line widely used for the study of the metabolic process of adipocytes, and as the cells actively differentiate, fat is also actively accumulated. The cell line obtained from American Type Culture Collection (ATCC) was Dulbecco's modified Eagle's medium (DMEM, Lonza, Allendale, N.J., USA) containing 10% Bovine calf serum (BCS, Gibco, Grand Island, N.Y., USA) and 1% penicillin-streptomycin (P/S, Gibco, Grand Island, N.Y., USA), and it was incubated under the maintained condition of 37° C. and 5% $CO_2$.

Stabilized 3T3-L1 preadipocytes were inoculated in $1 \times 10^5$ cells/ml density on a 24 well plate and cultured, and kept for additional 2 days when 100% confluent is reached. Further, differentiation of adipocyte was induced for 2 days using 10% Fetal Bovine Serum (FBS, Gibco, Grand Island, N.Y., USA) DEME medium comprising 0.5 mM IBMX (3-isobutyl-1-methylzanthine, Sigma, St. Louis, Mo., USA), 104 Dexamethasone (Sigma, St. Louis, Mo., USA), and 10 µg/ml Insulin (Gibco, Grand Island, N.Y., USA). After the 2-day incubation, it was incubated for 2 more days using 10% FBS DMEM medium comprising 10 µg/ml Insulin. Afterwards, it was incubated for 4 days while replacing the 10% FBS DMEM medium every 2 days.

During the differentiation process to the adipocyte, *Gynostemma Pentaphyllum* leaves extracts were treated in each culture solution with the density of 4, 20, 100 µl/ml, respectively, and the degree of adipocyte differentiation was observed on the $10^{th}$ day, when the differentiation is complete.

Experimental Example 3-2

Oil Red O Staining

To determine whether *Gynostemma Pentaphyllum* leaves extracts obtained in the above working examples or comparative examples inhibit adipocyte differentiation of 3T3-L1 preadipocytes and adipogenesis, Oil Red O Staining that specifically stains neutral lipids was performed.

Specifically, after the medium was eliminated from the cell from which adipocyte differentiation was induced, it was fixed at room temperature for 30 minutes using 4% formaldehyde after washing 2 times with PBS (Phosphate Buffered Saline). After fixation, it was washed with 60% isopropanol, and stained at room temperature for an hour using 0.2% oil red O dye (dissolved in 60% isopropanol).

Following the staining, it was washed with distilled water and observed with an optical microscope. In addition, the stained cell was dissolved by isopropanol and its absorbance was measured at 570 nm using ELIZA reader.

Figure 3:
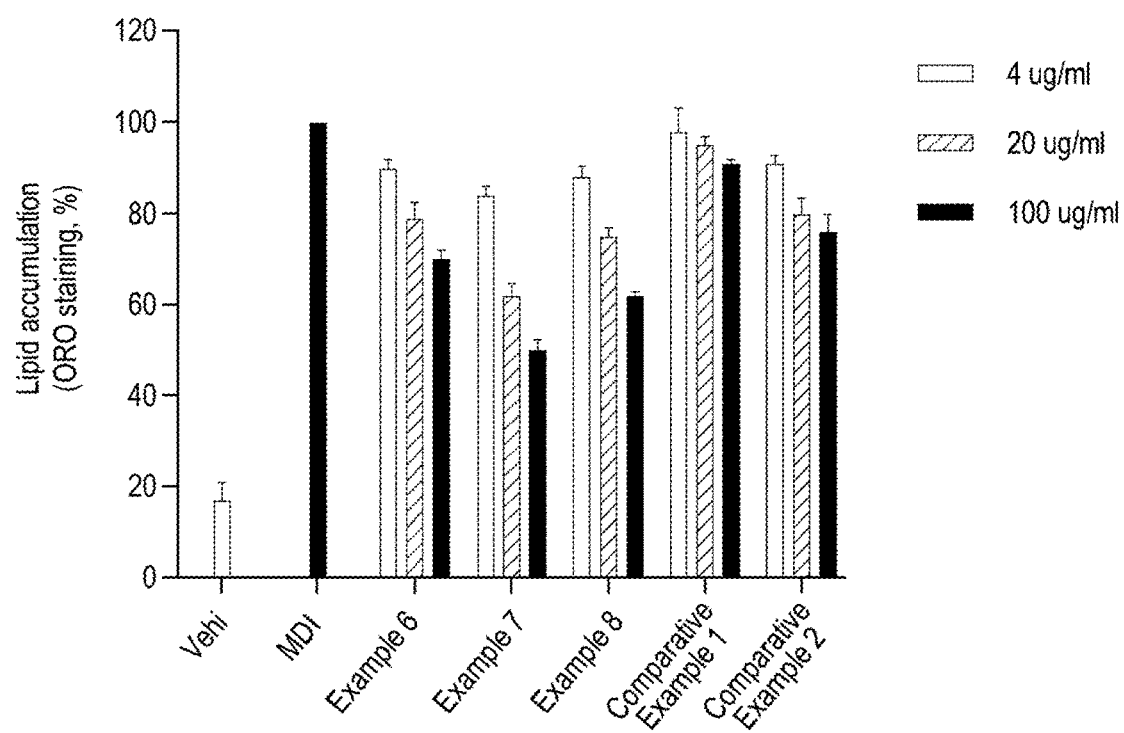
FIG. 3 is a graph showing the lipid accumulation rate in 3T3-L1 preadipocytes treated with Gynostemma Pentaphyllus leaves extract according to the working examples and comparative examples of the present invention.

Equation 2 was used to calculate the fat accumulation rate in an adipocyte, and the result is shown in FIG. 3.

Fat accumulation rate (%)=(Absorbance of the tested sample/Absorbance of control)×100 [Equation 2]

FIG. 3 is a graph showing the rate of lipid accumulation in an 3T3-L1 adipocyte treated with *Gynostemma Pentaphyllum* leaves extracts according to the working examples and the comparative examples of the present invention. As shown in FIG. 3, *Gynostemma Pentaphyllum* leaves extracts of Examples 1 and 2 exhibited 45% and 52% MDI neutral fat accumulation rates, respectively, and showed statistically significant differences. Further, the working examples treated with the *Gynostemma Pentaphyllum* leaves extracts of the working examples showed more reduced fat accumulation rate as compared to the comparative examples.

Therefore, the *Gynostemma Pentaphyllum* leaves extracts of the present invention is confirmed to show preventive or treatment effect for obesity by effectively inhibiting the adipocyte differentiation of preadipocytes and the production of neutral fat, as well as a high yield rate for easy industrialization.

Experimental Example 4

Effect of Increasing AMPK Phosphorylation

ACC is an important enzyme which regulates lipid metabolism in liver and muscles. The enzyme carboxylates acetyl-CoA to produce malonyl-CoA. Malonyl-CoA is the most important factor that controls the beta oxidation of fatty acids within the mitochondria. When the malonyl-CoA levels increase, the activity of CPT-1 (carnitine palmitoyl-CoA transferase) is reduced, and thus the oxidation of fatty acids is inhibited; and when the malonyl-CoA levels decrease, beta oxidation is increased and a decrease in body fat is stimulated. ACC is a sub-target protein for AMPK activation, and AMPK activation accelerates the inactivation of the ACC enzyme, thereby reducing the level of malonyl-CoA by phosphorylation of the ACC. As a result, beta oxidation of fatty acids increases due to the increase in CPT-1 activation in the mitochondrial membrane.

Figure 4:
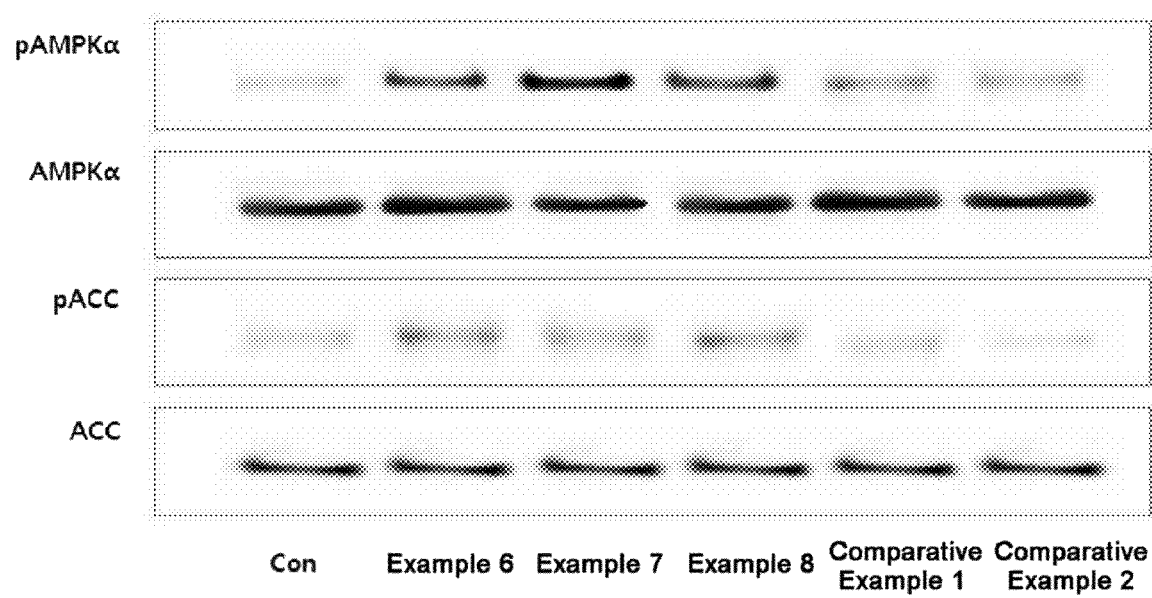
FIG. 4 is a photograph showing an effect of increasing AMPK and ACC phosphorylation in a L6 myotube cell treated with Gynostemma Pentaphyllus leaves extract according to the working examples and comparative examples of the present invention.

Accordingly, AMPK phosphorylation increasing effect of the *Gynostemma Pentaphyllum* leaves extracts of the working examples and the comparative examples was examined. L6 myotube cells were treated with each of *Gynostemma Pentaphyllum* leaves extract for two hours. The increased extent of the phosphorylation of a threonine residue at Thr-172 of AMPK a subunit and a serine residue at Ser-79 of an ACC enzyme protein were analyzed through western blot analysis according to the method of Hwang, et al. (Biochem. Biophys. Res. Commun. 371, 289-293, 2008). As a result, the treatment with *Gynostemma Pentaphyllum* leaves extracts was confirmed to increase the phosphorylation of AMPK and ACC, respectively, within the L6 myotube cells compared to the control group (see FIG. 4).

Experimental Example 5

Effect of AMPK Activation

AMK activation effect of the *Gynostemma Pentaphyllum* leaves extracts of the present invention was analyzed using 3T3-L1 cells.

First, 3T3-L1 cells were inoculated on a 6 well plate, and cultured with DMEM medium comprising 10% BSC. The medium was then changed to DMEM medium comprising 1% FBS to induce differentiation.

After harvesting the above with SDS sample buffer, protein lysate was obtained through sonication. Further, the protein was transferred to PVDF transfer membrane by conducting a 10% SDS-PAGE electrophoresis and using a semi-dry transfer device. The above transferred protein was gone through blocking process with 5% skim milk at the room temperature for an hour, which was then incubated over night at 4° C. using total AMPK and phosphor-AMPK (Thr172) antibody. This was then washed 3 times with TBS buffer to which 0.1% tween-20 had been added, and an immunoblot was conducted using anti-mouse HRP secondary antibody. Increase in AMPK activity during energy metabolism is known to increase the phosphorylation of the ACCs (acetyl-CoA carboxylase 1 and 2).

Figure 5:
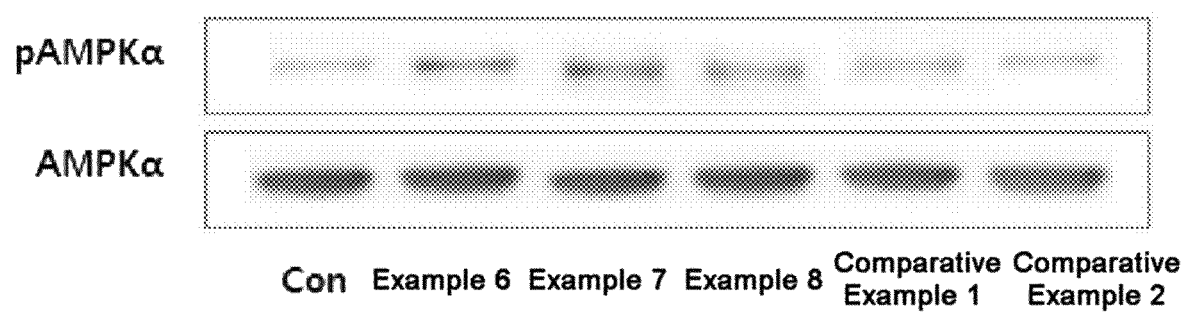
FIG. 5 is a photograph showing AMPK activation in 3T3-L1 preadipocyte treated with Gynostemma Pentaphyllus leaves extract according to the working examples and comparative examples of the present invention.

The AMPK activating action of the 3T3-L1 cells treated with the *Gynostemma Pentaphyllum* leaves extracts of the working examples is shown in FIG. 5. As can be seen from FIG. 5, the cells treated with the *Gynostemma Pentaphyllum* leaves extracts of the working examples showed strong AMPK activity.

Experimental Example 6

Fat Reducing Effect Through the Acceleration of Beta Oxidation

Effect of increasing the beta oxidation of fatty-acids was examined by treating the *Gynostemma Pentaphyllum* leaves extracts according to the working examples and the comparative examples to the incubated L6 myotube cells with the method of Hwang et al. (Hwang et al., Biochem. Biophys. Res. Commun. 377, 1253-1258).

Figure 6:
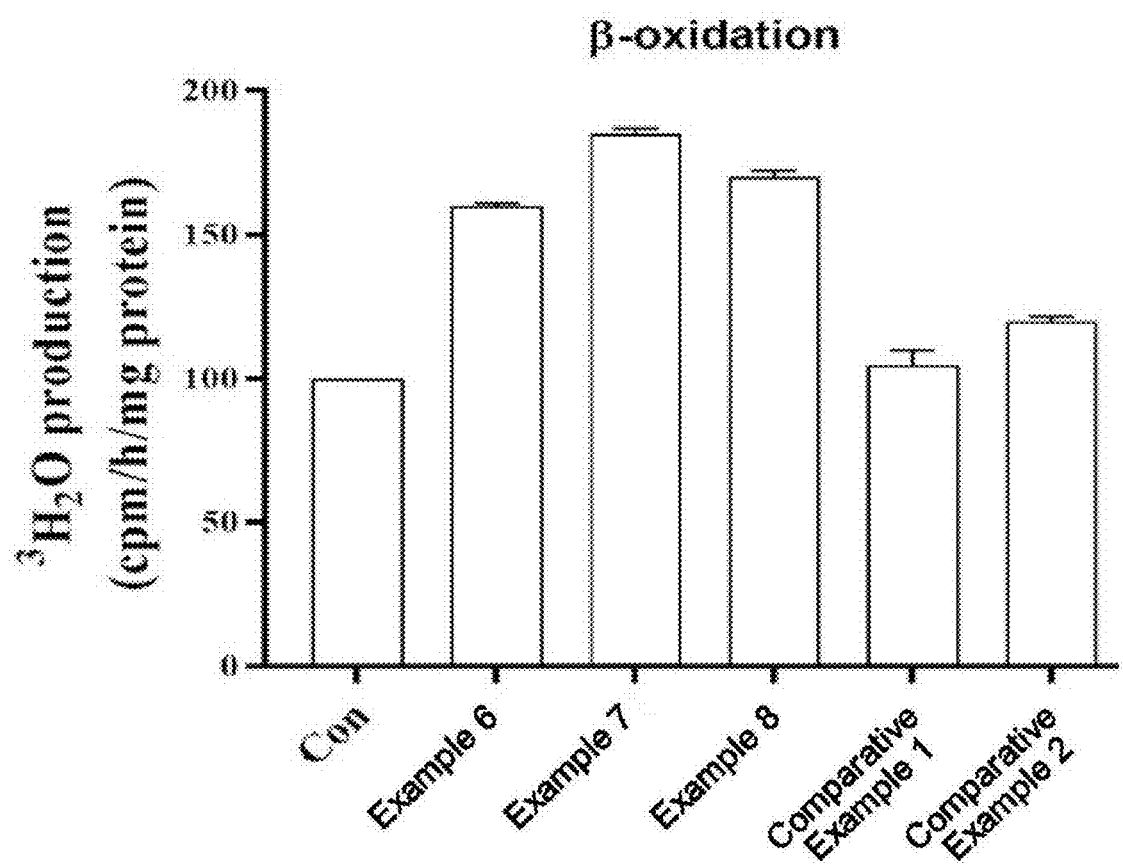
FIG. 6 is a graph showing an effect of accelerating beta oxidation of fatty acids of Gynostemma Pentaphyllus leaves extract according to the working examples and comparative examples of the present invention.

As a result, beta oxidation was observed to be increased with treatment from the *Gynostemma Pentaphyllum* leaves extracts according to the present invention. The results are shown in FIG. 6.

Experimental Example 7

Accelerating Effect of Glucose Absorption

The impact on glucose absorption was examined by treating the *Gynostemma Pentaphyllum* leaves extracts according to the working examples and the comparative examples to L6 myotube cells. To the cultured L6 myotube cells, high concentration glucose was added together with 2-DG (2-deoxy-[3H]D-glucose) (a radioactive isotope that does not decompose within a cell) according to the method of Hwang et al. (Biochem. Biophys. Res. Commun. 377, 1253-1258). The extent of acceleration of 2-DG absorption into the cells by the *Gynostemma Pentaphyllum* leaves extracts was then examined.

Figure 7:
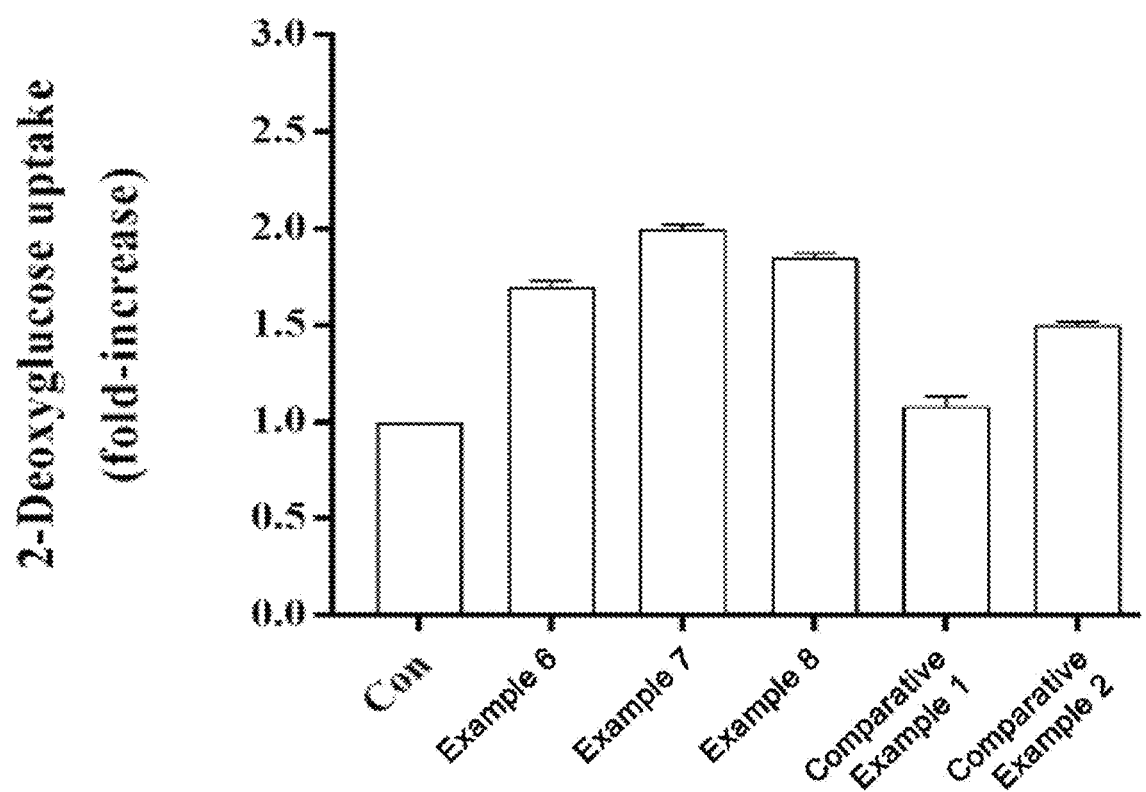
FIG. 7 shows a graph showing a glucose uptake acceleration effect in a cell of Gynostemma Pentaphyllus leaves extract according to the working examples and comparative examples of the present invention

As a result, the cells which were treated with *Gynostemma Pentaphyllum* leaves extracts of the present invention showed enhanced ability of glucose uptake (FIG. 7). According to the above, *Gynostemma Pentaphyllum* leaves extracts of the present invention are confirmed to have superior antidiabetic effect through its hypoglycemic effect.

Experimental Example 8

Effects of Activating Muscle Generation and Inhibiting Muscle Breakdown

When phosphorylated, the mTOR protein is known to induce the activation of proteins involved in the synthesis of muscle protein resulting in increased muscle mass via the PI3K/Akt signaling pathway within the muscle cells. Accordingly, to examine this muscle generation-inducing activity, *Gynostemma Pentaphyllum* leaves extracts of the working examples and the comparative examples were treated according to the method of Hwang et al. (Biochem. Biophys. Res. Commun. 377, 1253-1258). On the $8^{th}$ day, when the differentiation was completed, the degree of the muscle cells' differentiation was measured using the image J program.

Figure 8:
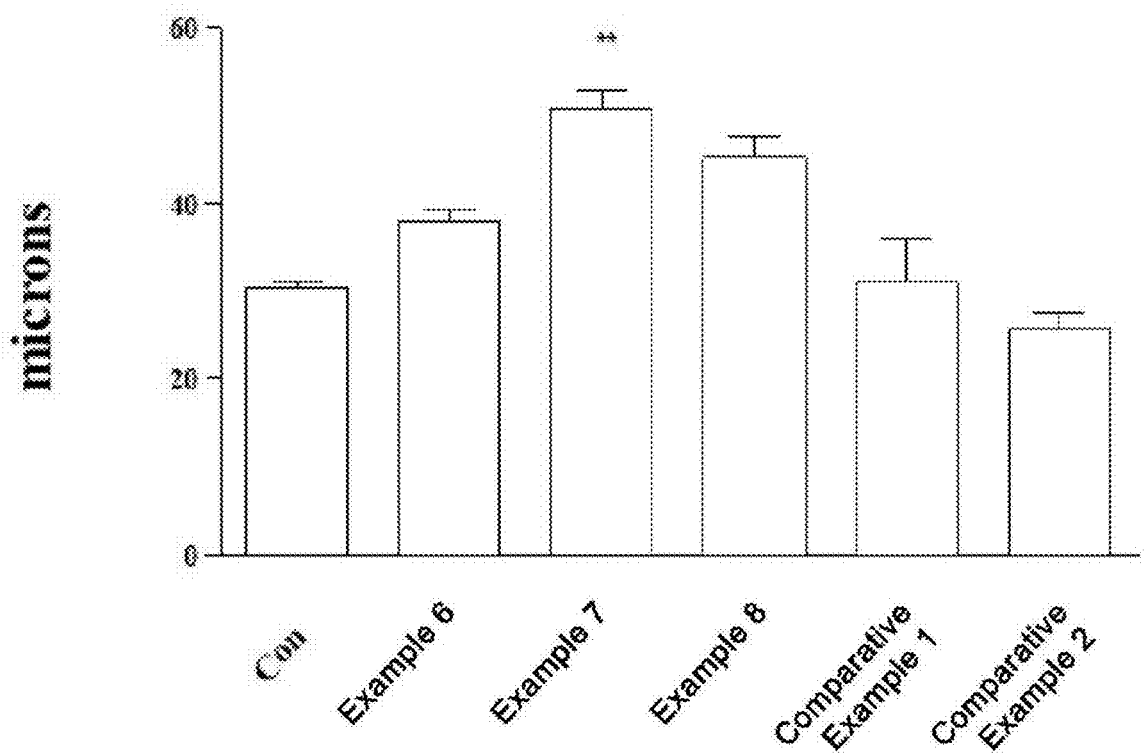
FIG. 8 is a graph showing an effect of inducing muscle cell differentiation of the Gynostemma Pentaphyllus leaves extracts according to the working examples and comparative examples of the present invention.

As a result, as shown in FIG. 8, after treatment with the *Gynostemma Pentaphyllum* leaves extracts, the differentiation of L6 myotube cells was confirmed to have significantly increased compared to the control group. After the induction of muscle differentiation, the protein was extracted and its expression levels of mTOR and MURF-1 were measured and are shown in FIGS. 9 and 10.

Figure 9:
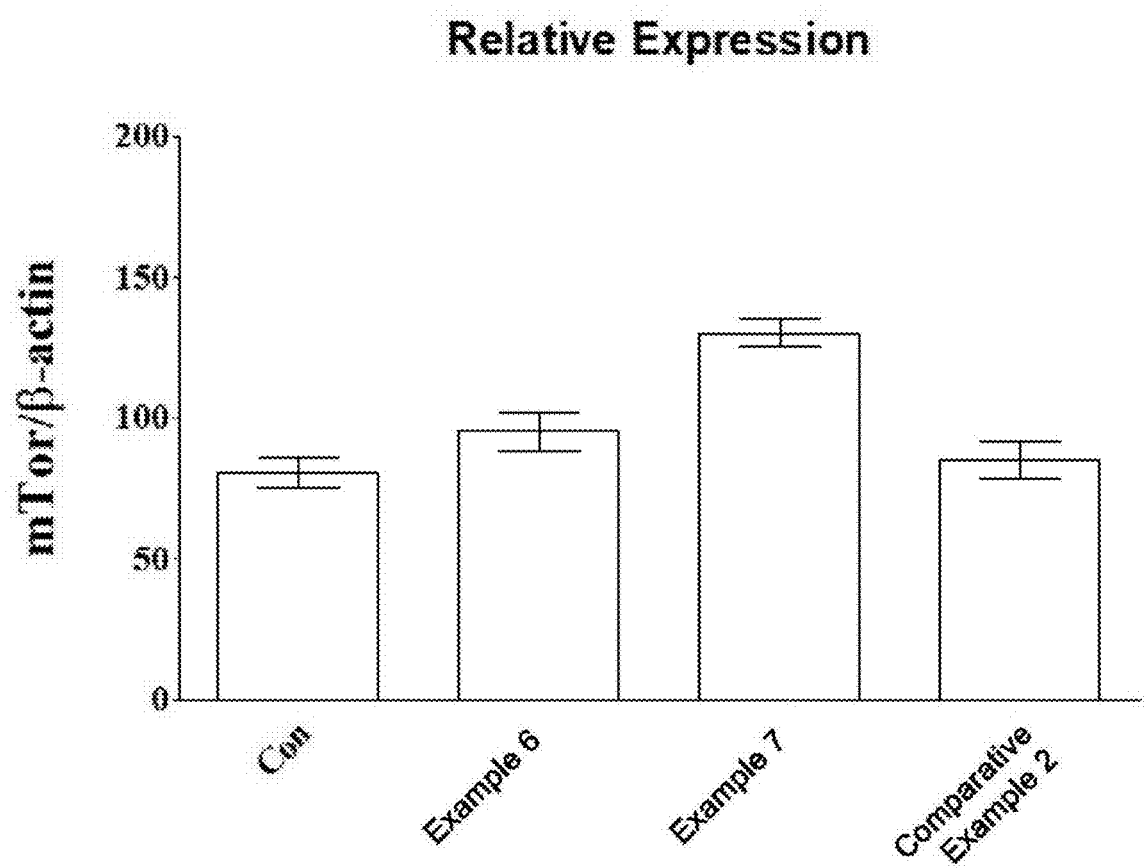
FIG. 9 is a graph showing the amount of mTOR in muscle cell line expressed by the Gynostemma Pentaphyllus leaves extracts according to the working examples and comparative examples of the present invention.
Figure 10:
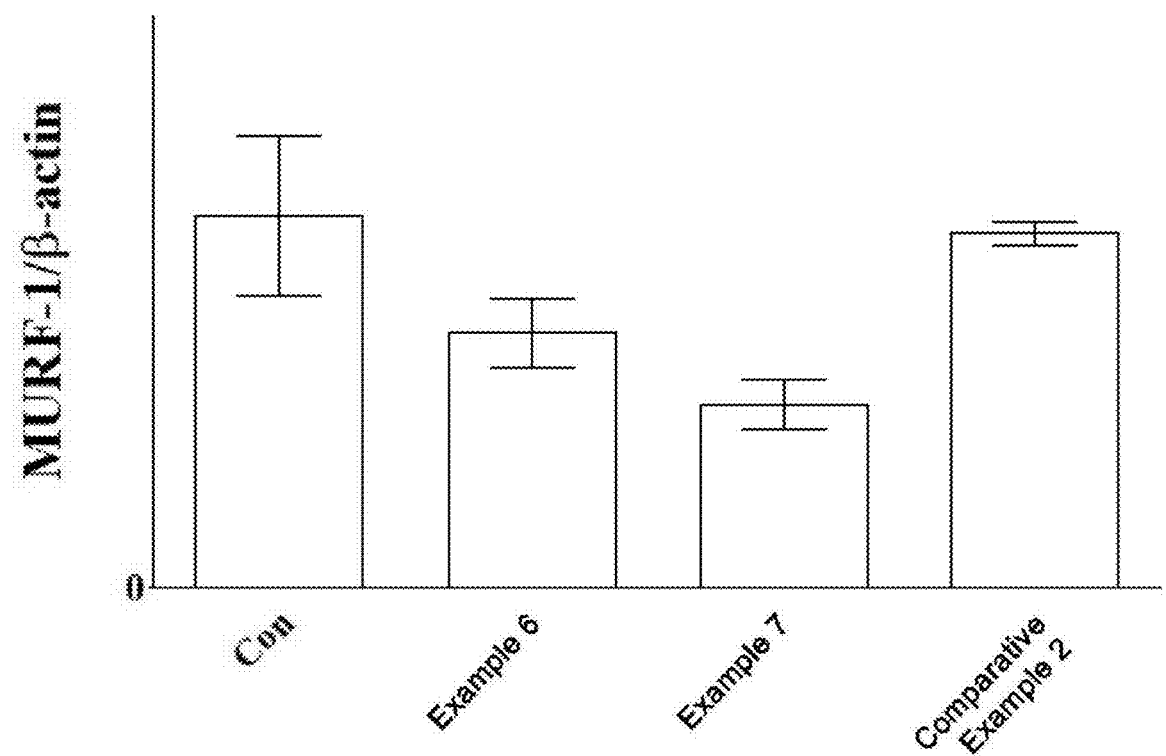
FIG. 10 is a graph showing the amount of MURF-1, a biomarker for acceleration of muscle breakdown, in muscle cell line, expressed by the Gynostemma Pentaphyllus leaves extracts according to the working examples and comparative examples of the present invention.

As can be seen from FIG. 9, the results show that the mTOR activity in L6 myotube cells were increased significantly (**$P<0.01$) from the treatment with the *Gynostemma Pentaphyllum* leaves extracts. Further, as shown in FIG. 10, MURF-1 activity in the L6 myotube cells was significantly (**$P<0.01$) reduced after treatment with the *Gynostemma Pentaphyllum* leaves extracts. This means that the *Gynostemma Pentaphyllum* leaves extracts of the present invention have excellent ability to increase muscle generation and inhibit muscle breakdown within the muscle cells.

Experimental Example 9

Effect of Increasing Motor Performance Ability

After accommodating male ICR mice (30 g) obtained from Coatech (Republic of Korea) to 12-hour light/dark cycles at 22-24° C. and 40-60% RH, 8 mice were placed into each of the following experimental groups: Experimental group 1 (motor control group; hereinafter referred to as "NC"); Experimental group 2 (Example 7); Experimental group 3 (Comparative Example 2) (the testing material was administered once daily for 4 weeks).

Figure 11:
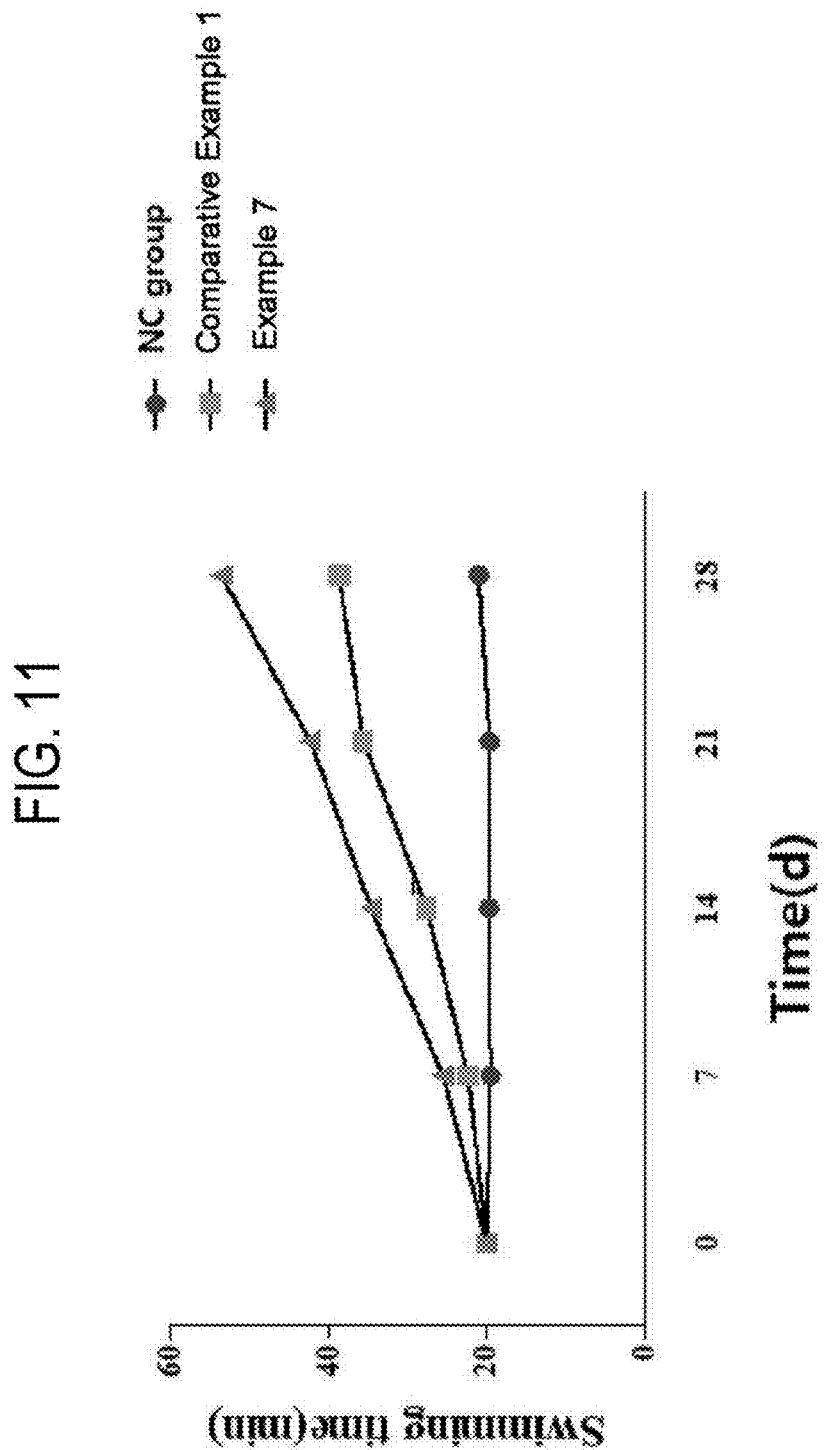
FIG. 11 is a graph which measured the motor ability (endurance) by treating the Gynostemma Pentaphyllus leaves extracts according to the working examples and comparative examples of the present invention.

The test animals were kept in the breeding condition of stable state from 16 hours before the start of the experiment, and exercised in acrylic plastic pool (70 cm, 70 cm, 60 cm) of which 70% is filled with water. Observation of no further movement due to the exhaustion of the test animals was accepted as the end point, and the swimming time was measured from the starting point to the end point. As shown in FIG. 11, the swimming time until the exhaustion was measured to determine the motor performance ability. The results show that the motor performance ability of the Example 7 group was enhanced compared to that of the control group, and in particular, that its motor performance ability was excellent, since the swimming time was the longest when also compared to the comparative example group.

FORMULATION EXAMPLES

Formulation Example 1

Preparation of Tablets 8 mg of *Gynostemma Pentaphyllum* leaves extracts of Examples 1 or 2, 9 mg of Vitamin E, 9 mg of Vitamin C, 200 mg of galacto-oligosaccharide, 60 mg of lactose, and 140 mg of maltose were mixed, granulated using a fluidized bed dryer, and then 6 mg of sugar ester was added thereto. 500 mg of the above composition was prepared as a tablet by a general tablet compression method.

Formulation Example 2

Soft Capsules

According to a general preparation method for soft capsules, a soft capsule was prepared by mixing 8 mg of *Gynostemma Pentaphyllum* leaves extracts of Examples 1 or 2, 9 mg of Vitamin C, 2 mg of palm oil, 8 mg of hydrogenated vegetable oil, 4 mg of yellow wax, and 9 mg of lecithin. The soft capsules were prepared by filling the mixture into a gelatin capsule.

Formulation Example 3

Preparation of Drinks

After mixing 8 mg of *Gynostemma Pentaphyllum* leaves extracts of Examples 1 or 2, 9 mg of Vitamin E, 9 mg of Vitamin C, 10 mg of glucose, 0.6 mg of citric acid, and 25 mg of liquid oligosaccharide, 300 ml of purified water was added thereto. Each bottle was filled with the mixture until 200 ml. After being filled, the bottles were sterilized at 130 r for 4-5 seconds, and thus, the drinks were prepared.

Formulation Example 4

Granules

Granules were prepared by mixing 8 mg of *Gynostemma Pentaphyllum* leaves extracts of Examples 1 or 2, 9 mg of Vitamin E, 9 mg of Vitamin C, 250 mg of crystalline anhydride glucose, and 550 mg of starch, moulded into granules by using a fluidized bed granulator, and then filling into a sheet.

Formulation Example 5

Injections

In accordance with the composition disclosed in Table 8 below, injections were prepared by a general method.

TABLE 8

| Combined components | Contents |
| --- | --- |
| *Gynostemma Pentaphyllum* leaves extracts of Examples 1 and 2 | 10-50 mg |
| Sterile, distilled water for injection | Proper amount |
| pH regulator | Proper amount |

Formulation Example 6

Preparation of Health Drinks

In accordance with the composition disclosed in Table 8 below, health drinks were prepared by a general method.

TABLE 9

| Combined components | Content |
| --- | --- |
| *Gynostemma Pentaphyllum* leaves extracts of Examples 1 and 2 | 20 mg |
| Vitamin A acetate | 70 ug |
| Vitamin E | 1.0 mg |
| Vitamin B1 | 0.13 mg |
| Vitamin B2 | 0.15 mg |

According to a general health drink preparation method, after mixing the above components, the mixture was then stirred and heated at 85° C. for about an hour. Thus-obtained solution was filtered and sterilized.

Formulation Method 7

Preparation of Health Care Foods

In accordance with the composition disclosed in Table 10 below, health care foods were prepared by a general method.

TABLE 10

| Mixed Components | contents |
| --- | --- |
| *Gynostemma Pentaphyllum* leaves extracts of Examples 1 and 2 | 20 mg |
| Vitamin A acetate | 70 ug |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 ug |
| Vitamin C | 10 mg |
| Biotin | 10 ug |
| Nicotine acid amide | 1.7 mg |
| Folic acid | 50 ug |
| Calcium pantothenate | 0.5 mg |
| Ferrous sulfate | 1.75 mg |
| Zinc oxide | 0.82 mg |
| Magnesium carbonate | 25.3 mg |
| Potassium phosphate | 15 mg |
| Potassium diphosphate | 55 mg |
| Potassium citrate | 90 mg |
| Potassium carbonate | 100 mg |
| Magnesium chloride | 24.8 mg |

Although the composition ratio of vitamins and mineral mixture above was composed according to a preferable working example relatively suitable for a health care food, the mixing ratio can be randomly modified.

*Gynostemma Pentaphyllus* leaves extract prepared according to the present invention is characterized in that the large amount of the small molecular effective saponin which are mainly ginsenoside Rg3, gypenoside L, gypenoside LI, etc., is obtained and low amount of benzopyrene is produced.

Further, since the above *Gynostemma Pentaphyllus* leaves extract shows efficacy such as increase in AMPK activation, acceleration of beta oxidation, stimulation of glucose uptake, etc., it shows an effect of preventing or treating diabetes, obesity, muscle loss, etc. and improving motor ability.

From the above explanations, those skilled in the technical field to which the present invention belongs will understand that the present invention can be worked in other specific embodiments without modifying its technical idea or essential features. In this regard, the working examples should be understood as illustrative and not limiting in every aspect. The scope of the present invention should be interpreted according to the meanings and scope of the claims provided below and all modified and transformed embodiments deduced from their equivalents, rather than the detailed descriptions above.

What is claimed is:

1. A preparation method of *Gynostemma Pentaphyllum* leaves extracts comprising the steps of:
   (1) drying fresh *Gynostemma Pentaphyllum* leaves after roasting or steaming;
   (2) treating the dried *Gynostemma Pentaphyllum* leaves with steam;
   (3) adding water of 1 to 100-fold volume to the above *Gynostemma Pentaphyllum* leaves and then preparing a hot water extract by carrying out a hot water extraction at 100-150° C., 1-10 atm for 0.5-120 hours, followed by collecting the hot water extract;
   (4) adding $C_1$-$C_4$ lower alcohol of 1 to 100-fold volume to the residual remained after the hot water extraction and then preparing an alcohol extract of the residual from the hot water extract by carrying out an alcohol extraction at 50-100° C. for 1-120 hours, followed by collecting the alcohol extract; and
   (5) mixing the hot water extract of step (3) and the alcohol extract of step (4), and then filtering and concentrating the mixture.

2. The preparation method of *Gynostemma Pentaphyllum* leaves extracts according to claim 1,
   wherein the roasting in step (1) is carried out at 90-300° C. for 1-120 hours.

3. The preparation method of *Gynostemma Pentaphyllum* leaves extracts according to claim 1,
   wherein the steaming in step (1) is carried out at 90-180° C. for 1-120 hours.

4. The preparation method for *Gynostemma Pentaphyllum* leaves extracts according to claim 1,
   wherein the steam treatment in step (2) is carried out for 0.5-10 hours.

5. The preparation method for *Gynostemma Pentaphyllum* leaves extracts according to claim 1,
   wherein the process of roasting the steam-treated *Gynostemma Pentaphyllum* leaves at 90-180° C. for 1-120 hours using an electric heater, drying the leaves, and treating them with steam at 100-130° C. for 0.5-10 hours is repeatedly carried out 1 to 5 times after step (1) and step (2) are completed.

6. The preparation method for *Gynostemma Pentaphyllum* leaves extracts according to claim 1,
   wherein the $C_1$-$C_4$ lower alcohol in the preparation step of the alcohol extract is one or more selected from methanol, ethanol, propanol, isopropanol, and butanol.

7. The preparation method for *Gynostemma Pentaphyllum* leaves extracts according to claim 1,
   wherein the lower alcohol in the preparation step of the alcohol extract is an alcohol aqueous solution of 10-95%(v/v), respectively.

8. The preparation method for *Gynostemma Pentaphyllum* leaves extracts according to claim 1,
   wherein the pH of the water of step (3) and the $C_1$-$C_4$ lower alcohol of step (4) used for the extraction is in the range from pH 0 to pH 7.

9. The preparation method for *Gynostemma Pentaphyllum* leaves extracts according to claim 7,
   adding one or more from citric acid, butyric acid, hydrochloric acid, trifluoroacetic acid, trichloroacetic acid, acetic acid, vitamin C, malic acid, lactic acid, succinic acid, alginate to regulate the pH of water of step (3) and the $C_1$-$C_4$ lower alcohol of step (4).

10. The preparation method for *Gynostemma Pentaphyllum* leaves extracts according to claim 1,
    wherein the *Gynostemma Pentaphyllum* leaves extracts comprise 0.01~7 mg/g of ginsenoside Rg3, 1.5~70 mg/g of gypenoside L, and 1.5~70 mg/g of gypenoside LI.

11. The preparation method for *Gynostemma Pentaphyllum* leaves extracts according to claim 1,
    wherein the *Gynostemma Pentaphyllum* leaves extracts comprise 10 or less ppb benzopyrene.

* * * * *